United States Patent
Lamb et al.

(10) Patent No.: US 10,793,867 B2
(45) Date of Patent: Oct. 6, 2020

(54) METHODS FOR TARGETED TRANSGENE-INTEGRATION USING CUSTOM SITE-SPECIFIC DNA RECOMBINASES

(71) Applicant: Monsanto Technology, LLC, St. Louis, MO (US)

(72) Inventors: Jonathan C. Lamb, Wildwood, MO (US); Richard J. Lawrence, Kirkwood, MO (US)

(73) Assignee: Monsanto Technology, LLC, St. Louis, MO (US)

(*) Notice: Subject to any disclaimer, the term of this patent is extended or adjusted under 35 U.S.C. 154(b) by 580 days.

(21) Appl. No.: 14/209,828

(22) Filed: Mar. 13, 2014

(65) Prior Publication Data

US 2015/0167010 A1   Jun. 18, 2015

Related U.S. Application Data

(60) Provisional application No. 61/793,722, filed on Mar. 15, 2013, provisional application No. 61/801,991, filed on Mar. 15, 2013.

(51) Int. Cl.
*C12N 15/82* (2006.01)
*C12Q 1/6895* (2018.01)
*C12N 9/22* (2006.01)

(52) U.S. Cl.
CPC .......... *C12N 15/8213* (2013.01); *C12N 9/22* (2013.01); *C12Q 1/6895* (2013.01)

(58) Field of Classification Search
None
See application file for complete search history.

(56) References Cited

U.S. PATENT DOCUMENTS

| | | | |
|---|---|---|---|
| 6,580,019 B1 | 6/2003 | McElroy et al. | |
| 6,750,379 B2 | 6/2004 | McElroy et al. | |
| 7,736,897 B2 * | 6/2010 | Tao | C12N 15/1051 435/419 |
| 7,919,321 B2 | 4/2011 | Flasinski | |
| 8,450,107 B1 * | 5/2013 | Zhang | C12N 5/0686 435/325 |
| 9,708,589 B2 | 7/2017 | Lamb et al. | |
| 2001/0056583 A1 | 12/2001 | McElroy et al. | |
| 2005/0060769 A1 | 3/2005 | Gilbertson | |
| 2008/0178348 A1 | 7/2008 | Gilbetson | |
| 2010/0086532 A1 * | 4/2010 | Barbas, III | C12N 15/1082 424/94.5 |
| 2011/0126310 A1 | 5/2011 | Feng et al. | |
| 2011/0145940 A1 | 6/2011 | Voytas et al. | |
| 2011/0239315 A1 * | 9/2011 | Bonas | C12N 15/1034 800/13 |
| 2011/0301073 A1 | 12/2011 | Gregory et al. | |
| 2012/0110685 A1 | 5/2012 | Bonas et al. | |
| 2012/0178131 A1 | 7/2012 | Voytas et al. | |
| 2012/0178169 A1 | 7/2012 | Voytas et al. | |
| 2012/0192301 A1 | 7/2012 | Jaenisch et al. | |
| 2012/0214228 A1 | 8/2012 | Voytas et al. | |
| 2012/0222143 A1 | 8/2012 | Fahrenkrug et al. | |
| 2013/0137173 A1 | 5/2013 | Feng et al. | |
| 2014/0283166 A1 | 9/2014 | Chomet et al. | |
| 2015/0203871 A1 | 7/2015 | Juillerat et al. | |
| 2015/0218230 A1 | 8/2015 | Juillerat et al. | |
| 2015/0284728 A1 | 10/2015 | Barbas, III et al. | |
| 2018/0023062 A1 | 1/2018 | Lamb et al. | |

FOREIGN PATENT DOCUMENTS

WO   WO 2001/066780   9/2001

OTHER PUBLICATIONS

Gersbach et al 2010 (Nucleic Acids Research 38:12 p. 4198-4206).*
Ow 2011 (Journal of Integrative Plant Biology 53:7 p. 512-519).*
Louwerse et al 2007 (Plant Physiology 145: p. 1282-1293).*
Response to Non-Final Office Action regarding U.S. Appl. No. 14/109,823, dated Jul. 25, 2016.
USPTO: Final Office Action regarding U.S. Appl. No. 14/109,823, dated Nov. 3, 2016.
U.S. Appl. No. 14/209,731, filed Mar. 13, 2014, Chomet et al.
U.S. Appl. No. 14/109,823, filed Dec. 14, 2013, Lamb et al.
Akopian et al., "Chimeric recombinases with designed DNA sequence recognition;" *Proc Natl Acad Sci USA* 100(15):8688-91, 2003.
Boch et al., "Breaking the code of DNA binding specificity of TAL-type III effectors," *Science* 326:1509-1512, 2009.
Bogdanove et al., "TAL Effectors: Customizable Proteins for DNA Targeting," *Science* 333:1843-1846, 2011.
Broothaerts et al., "Gene transfer to plants by diverse species of bacteria," *Nature* 443(7026):629-633, 2005.
Bruce et al., "Influence of retinoblastoma-related gene silencing on the initiation of DNA replication by African cassava mosaic virus Rep in cells of mature leaves in *Nicotiana benthamiana* plants," *Virol J.* 8:561, 2011.
Buchholz et al., "In vitro evolution and analysis of HIV-1 LTR-specific recombinases," *Methods* 53(1):102-109, 2011.
Deng et al., "Structural Basis for Sequence-Specific Recognition of DNA by TAL Effectors," *Science* 335:720-723, 2012.

(Continued)

*Primary Examiner* — Matthew R Keogh
(74) *Attorney, Agent, or Firm* — Dentons US LLP; Amanda Carmany-Rampey

(57) ABSTRACT

The invention relates to biotechnology and provides novel methods for sequence-specific or sequence-directed transcription activator-like effector recombinase-mediated integration of DNA sequences of interest into host genomes. The invention also provides methods of use for novel plant transformation vectors and expression cassettes, which include novel combinations of chimeric recombinases with plant expression and transformation elements. Methods for gene-targeting, DNA sequence removal, genome modification, and molecular breeding are also provided.

42 Claims, 5 Drawing Sheets

Specification includes a Sequence Listing.

(56) References Cited

OTHER PUBLICATIONS

Dhar et al., "Architecture of the Hin Synaptic Complex during Recombination," *Cell* 119(1):33-45, 2004.
Gaj et al., "Structure-guided reprogramming of serine recombinase DNA sequence specificity," *Proc Natl Acad Sci USA* 108(2):498-503, 2011.
Garcia-Otin et al., "Mammalian genome targeting using site-specific recombinases," *Frontiers in Bioscience* 11:1108-1136, 2006.
Gelvin, "Agrobacterium-Mediated Plant Transformation: the Biology behind the 'Gene-Jockeying' Tool," *Microbiology and Molecular Biology Reviews* 67(1):16-37, 2003.
Gersbach et al., "Directed evolution of recombinase specificity by split gene reassembly," *Nucleic Acids Res* 38(12):4198-4206, 2010.
Gordley et al., "Evolution of programmable zinc finger-recombinases with activity in human cells," *J Mol Biol* 367(3):802-13, 2007.
Gordley et al., "Synthesis of programmable integrases," *Proc Natl Aced Sci USA* 106(13):5053-5058, 2009.
Grindley et al., "Mechanisms of site-specific recombination," *Annu Rev Biochem* 75:567-605, 2006.
Hellens et al., "Technical Focus: A guide to Agrobacterium binary Ti vectors," *Trends in Plant Science* 5(10):446-451, 2000.
Hughes et al., "Sequence-specific interaction of the *Salmonella* Hin recombinase in both major and minor grooves of DNA," *EMBO J.* 11(7):2695-2705, 1992.
Iida et al., "A tale of two integrations, transgene and T-DNA: gene targeting by homologous recombination in rice," *Current Opinion in Biotechnology* 15(2):132-138, 2004.
Mak et al., "The Crystal Structure of TAL Effector PthXo I Bound to Its DNA Target," *Science* 335:716-719, 2012.
Mercer et al., "Chimeric TALE recombinases with programmable DNA sequence specificity," *Nucleic Acids Res* 40(21):11163-72, 2012.
Miki et al., "Procedures for introducing foreign DNA into plants," In: Methods in Plant Molecular Biology and Biotechnology, Glick et al. (Eds.), pp. 67-88, 1993.
Miller et al., "A TALE nuclease architecture for efficient genome editing," *Nat Biotechnol* 29(2):143-8, 2011.
Mor et al., "Geminivirus vectors for high-level expression of foreign proteins in plant cells," *Biotechnol Bioeng.* 81(4):430-7, 2003.
Moscou et al., "A Simple Cipher Governs DNA Recognition by TAL Effectors," *Science* 326:1501, 2009.
Nagy, "Cre recombinase: The universal reagent for genome tailoring," *Genesis* 26(2):99-109, 2000.
Nern et al., "Multiple new site-specific recombinases for use in manipulating animal genomes," *Proc Natl Acad Sci USA* 108(34):14198-203, 2011.
Proudfoot et al., "Zinc finger recombinases with adaptable DNA sequence specificity," *PLoS One* 6(4):e19537, 2011.
Rimphanitchayakit et al., "Saturation mutagenesis of the DNA site bound by the small carboxy-terminal domain of gamma delta resolvase," *EMBO J.* 9(3):719-725, 1990.
Schornack et al., "Gene-for-gene-mediated recognition of nuclear-targeted AvrBs3-like bacterial effector proteins," *J Plant Physiology* 163(3):256-272, 2006.
Smith et al., "Diversity in the serine recombinases," *Molecular Microbiology* 44(2):299-307, 2002.
Sun et al., "Optimized TAL effector nucleases (TALENs) for use in treatment of sickle cell disease," *Mol Biosyst* 8(4):1255-63, 2012.
Szurek et al., "Type III-dependent translocation of the Xanthomonas AvrBs3 protein into the plant cell," *Mol Microbiol* 46(1):13-23, 2002.
Torney et al., "Mesoporous silica nanoparticles deliver DNA and chemicals into plants," *Nature Nanotechnology* 2:295-300, 2007.
Turan et al., "Site-specific recombinases: from tag-and-target—to tag-and-exchange-based genomic modifications," *FASEB Journal*, 25:4088-4107, 2011.
Tucker et al., "Riboswitches as versatile gene control elements," *Current Opinion in Structural Biology* 15(3):342-348, 2005.
Vergunst et al., "VirB/D4-Dependent Protein Translocation from Agrobacterium into Plant Cells," *Science* 290(5493):979-982, 2000.
Willment et al., "Identification of long intergenic region sequences involved in maize streak virus replication," *J Gen Virol.* 88:1831-1841, 2007.
You et al., "Use of Bacterial Quorum-Sensing Components to Regulate Gene Expression in Plants," *Plant Physiology* 140(4):1205-1212, 2006.
Zhu et al., "Cleavage-dependent ligation by the FLP recombinase. Characterization of a mutant FLP protein with an alteration in a catalytic amino acid," *J. Biol Chem*, 270(30):23044-23054, 1995.
USPTO: Non-Final Office Action regarding U.S. Appl. No. 14/109,823, dated Feb. 25, 2016.
Response to Final Office Action regarding U.S. Appl. No. 14/109,823, dated Feb. 3, 2017.
USPTO: Notice of Allowance and Fees Due regarding U.S. Appl. No. 14/109,823, dated Mar. 9, 2017.
U.S. Appl. No. 15/633,591, filed Jun. 26, 2017, Lamb et al.
USPTO: Non-Final Office Action regarding U.S. Appl. No. 15/633,591, dated Jun. 14, 2018.
USPTO: Final Office Action regarding U.S. Appl. No. 15/633,591, dated Dec. 17, 2018.
Response to Final Office Action regarding U.S. Appl. No. 15/633,591, dated Apr. 17, 2019.
USPTO: Advisory Action regarding U.S. Appl. No. 15/633,591, dated Apr. 24, 2019.
Response to Office Action regarding U.S. Appl. No. 15/633,591, dated Dec. 6, 2019.
USPTO: Office Action regarding U.S. Appl. No. 15/633,591, dated Sep. 6,2019.
USPTO: Notice of Allowance and Fee(s) Due regarding U.S. Appl. No. 15/633,591, dated Apr. 22, 2020.
USPTO: Final Office Action regarding U.S. Appl. No. 15/633,591, dated Mar. 18, 2020.

\* cited by examiner

SEQUENCE LISTING

```
<160> NUMBER OF SEQ ID NOS: 10

<210> SEQ ID NO 1
<211> LENGTH: 90
<212> TYPE: DNA
<213> ORGANISM: Artificial Sequence
<220> FEATURE:
<223> OTHER INFORMATION: Recombinant

<400> SEQUENCE: 1
```

```
tagggacatg gtagtacgaa acgaagatag aacctacaca gcaatacgag aaatgtgtaa      60
tttggtgctt agcggtattt atttaagcac                                      90

<210> SEQ ID NO 2
<211> LENGTH: 70
<212> TYPE: DNA
<213> ORGANISM: Artificial Sequence
<220> FEATURE:
<223> OTHER INFORMATION: Recombinant

<400> SEQUENCE: 2
tcatactaca tgggtcaata gtatagggat tcatattata ggcgatacta taataatttg     60
ttcgtctgca                                                            70

<210> SEQ ID NO 3
<211> LENGTH: 90
<212> TYPE: DNA
<213> ORGANISM: Artificial Sequence
<220> FEATURE:
<223> OTHER INFORMATION: Recombinant

<400> SEQUENCE: 3
gtgggatgac gttaattggc tctgagcttc gtcctcttaa ggtcatgtct tctgtttcca     60
cggcgtgcat gctacacggt gcaagcagcc                                      90

<210> SEQ ID NO 4
<211> LENGTH: 66
<212> TYPE: DNA
<213> ORGANISM: Artificial Sequence
<220> FEATURE:
<223> OTHER INFORMATION: Recombinant

<400> SEQUENCE: 4
tggcatgatg aaggcaacat ggccatgatg aattcatcaa tcaagcttgg tacctctatt     60
aggtac                                                                66

<210> SEQ ID NO 5
<211> LENGTH: 70
<212> TYPE: DNA
<213> ORGANISM: Artificial Sequence
<220> FEATURE:
<223> OTHER INFORMATION: Recombinant

<400> SEQUENCE: 5
tagggacatg gtagtacgaa acgaatccaa aaccatggtt tacagtgctt agcggtattt     60
atttaagcac                                                            70

<210> SEQ ID NO 6
<211> LENGTH: 70
<212> TYPE: DNA
<213> ORGANISM: Artificial Sequence
<220> FEATURE:
<223> OTHER INFORMATION: Recombinant

<400> SEQUENCE: 6
tcatactaca tgggtcaata gtatatccaa aaccatggtt tacagtacta taataatttg     60
ttcgtctgca                                                            70

<210> SEQ ID NO 7
<211> LENGTH: 70
<212> TYPE: DNA
```

```
<213> ORGANISM: Artificial Sequence
<220> FEATURE:
<223> OTHER INFORMATION: Recombinant

<400> SEQUENCE: 7
gtgggatgac gttaattggc tctgatccaa aaccatggtt tacagtgcat gctacacggt    60
gcaagcagcc                                                           70

<210> SEQ ID NO 8
<211> LENGTH: 64
<212> TYPE: DNA
<213> ORGANISM: Artificial Sequence
<220> FEATURE:
<223> OTHER INFORMATION: Recombinant

<400> SEQUENCE: 8
tggcatgatg aaggcaacat ggccatccaa aaccatggtt tacagtggta cctctattag    60
gtac                                                                 64

<210> SEQ ID NO 9
<211> LENGTH: 20
<212> TYPE: DNA
<213> ORGANISM: Artificial Sequence
<220> FEATURE:
<223> OTHER INFORMATION: Recombinant
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (15)..(20)
<223> OTHER INFORMATION: n is a, c, g, or t

<400> SEQUENCE: 9
nnnnnnaccn nggtnnnnnn                                                20

<210> SEQ ID NO 10
<211> LENGTH: 20
<212> TYPE: DNA
<213> ORGANISM: Artificial Sequence
<220> FEATURE:
<223> OTHER INFORMATION: Recombinant
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (17)..(20)
<223> OTHER INFORMATION: n is a, c, g, or t

<400> SEQUENCE: 10
nnnnaaaccn nggtttnnnn                                                20
```

US 10,793,867 B2

METHODS FOR TARGETED TRANSGENE-INTEGRATION USING CUSTOM SITE-SPECIFIC DNA RECOMBINASES

CROSS REFERENCE TO RELATED APPLICATIONS

This application claims the benefit of U.S. Provisional Application No. 61/793,722, filed Mar. 15, 2013 and U.S. Provisional Application No. 61/801,991, filed Mar. 15, 2013, both of which are herein incorporated by reference in their entirety.

INCORPORATION OF SEQUENCE LISTING

The sequence listing that is contained in the file named "MONS330US.txt", which is 3,253 bytes (measured in MS-Windows) and created on Mar. 13, 2014, is filed herewith by electronic submission and incorporated herein by reference.

BACKGROUND OF THE INVENTION

Field of the Invention

The invention relates to the field of biotechnology.

Description of Related Art

Site-specific recombination has tremendous potential for application across a wide range of biotechnology-related fields. Zinc finger nucleases (ZFNs) are synthetic proteins, containing a DNA-binding domain and a DNA-cleavage domain, that have been successfully used to enable genome editing. Zinc finger recombinases (ZFRs) are made by fusing a recombinase catalytic domain to the N-terminus of a zinc finger (Akopian et al., 2003). Zinc fingers (ZFs) are just one among many different protein folds that enable proteins to bind DNA in a sequence-specific manner. Unfortunately, DNA targeting using zinc fingers is still limited by the difficulty in engineering novel DNA sequence specificities and site-specific recombination in unmodified genomes is only possible if recombinases can be designed to recognize endogenous target sequences with high specificity.

DNA-binding domains from transcription activator-like effector (TALE) proteins have a significant advantage over ZF domains as TALE protein DNA-binding domain specificity is determined by a straight-forward cipher allowing for the design of custom DNA-binding proteins.

SUMMARY OF THE INVENTION

In one aspect, the present invention provides a method for integrating a nucleic acid sequence into a genomic locus including transforming a host cell with at least one donor DNA construct. In some embodiments, the donor DNA construct includes a first TALE recombinase (TALER) target sequence and an exogenous DNA sequence. In particular embodiments, the method includes transforming the host cell with at least one nucleic acid sequence encoding a TALER. In one embodiment, the TALER forms part of a tetramer and mediates recombination between the first TALER target sequence and a second TALER target sequence located in the host cell genome. In other embodiments, the method includes identifying a transformed host cell including the donor DNA construct integrated at a selected genomic locus in said host cell.

In certain embodiments, the donor DNA construct further includes nucleic acid sequences that cause the formation of a circular intermediate comprising the exogenous DNA and the first TALER target sequence. In yet another embodiment, the nucleic acid sequences that cause the formation of a circular intermediate include flanking recombinase recognition sites. In particular embodiments, the flanking recombinase recognition sites are selected from the group consisting of Cre, FLP, phiC31, and TALER In some embodiments, the method further includes transforming a host cell with a nucleic acid sequence encoding a recombinase selected from the group consisting of Cre, FLP, phiC31, and TALER. In certain embodiments, the recombinase mediates recombination between the flanking recombinase recognition sites, thereby excising and circularizing an intermediate sequence including the exogenous DNA sequence and the first TALER target sequence. In particular embodiments, the excised and circularized intermediate sequence is integrated into the host cell genome by TALER-mediated recombination between the first and second TALER target sequences.

In particular embodiments, the nucleic acid sequences that cause the formation of a circular intermediate include viral sequences from a double-stranded DNA virus or a virus with a double-stranded DNA replication state. In one embodiment, the viral sequences include geminivirus or caulimovirus sequences. In other embodiments, the method further includes transforming a host cell with a nucleic acid sequence encoding a replication protein from the virus. In yet other embodiments, the replication protein mediates the formation of one or more double-stranded DNA intermediate circles including the exogenous DNA sequence and the first TALER target sequence. In still other embodiments, the one or more double-stranded DNA intermediate circles are integrated into the host cell genome by TALER-mediated recombination between the first and second TALER target sequences.

In one embodiment, the first and second TALER target sequences include a pair of TALE binding sites flanking a recombinase core sequence. In another embodiment, the pair of TALE binding sites is spaced from about 18 bp to about 50 bp apart.

In yet another embodiment, the donor DNA construct further includes a TALER expression construct. In one embodiment, the sequence encoding a TALER is a mRNA sequence. In some embodiments, transforming a host cell includes a method selected from the group consisting of biolistic particle bombardment, electroporation, and *Agrobacterium*-mediated transformation.

In certain embodiments, identifying a transformed host cell includes screening for integration of the donor DNA construct within the second TALER target sequence in the host cell genome. In particular embodiments, screening comprises PCR, DNA sequencing, or Southern blotting. In other embodiments, identifying a transformed host cell includes selecting for the host cell based on the expression of a selectable marker. In another embodiment, the selectable marker confers antibiotic resistance or herbicide tolerance.

In one embodiment, the donor DNA construct is circular or linear. In yet another embodiment, the TALER is selected from the group consisting of a specific N-terminal transcription activator-like effector recombinase protein (sN-TALER), a permissive N-terminal transcription activator-like effector recombinase protein (pN-TALER), a specific C-terminal transcription activator-like effector recombinase protein (sC-TALER), and a permissive C-terminal transcription activator-like effector recombinase protein (pC-TALER). In some embodiments, the TALER includes a small serine recombinase catalytic domain selected from the group consisting of Gin20H106Y, GinL7C7-EE2, GinL7C7-EE3, HinB (HinH106Y), and HinC. In certain embodiments, the method further includes regenerating a plant from said transformed host cell or a progeny therefrom. In particular embodiments, the plant includes the donor DNA construct integrated at a selected genomic locus.

In another aspect, the present invention provides a method for stacking transgenic loci including transforming a first host cell that includes a first transgenic locus at a first TALER target sequence in the first host cell genome. In yet another embodiment, the method includes transforming a first host cell with at least one donor circular DNA construct including a second TALER target sequence and a second transgenic locus.

In other embodiments, the method includes transforming a first host cell with at least one nucleic acid sequence encoding a TALER. In one embodiment, the TALER forms part of a tetramer and mediates recombination between the first TALER target sequence located in the first host cell genome and the second TALER target sequence located on the donor circular DNA construct. In a certain aspect, the method includes transforming a first host cell with at least one nucleic acid sequence encoding a selectable marker.

In particular embodiments, the method includes selecting a transformed first host cell expressing the selectable marker. In other embodiments, the method includes screening the selected transformed first host cell for integration of the donor circular DNA construct to identify a host cell of a subsequent generation that includes the first transgenic locus genetically linked to the second transgenic locus.

In another embodiment, the selectable marker confers antibiotic resistance or herbicide tolerance. In yet another embodiment, screening comprises PCR, DNA sequencing, or Southern blotting. In one embodiment, the steps of transforming a first host cell, selecting a transformed host cell, and screening the selected transformed first host cell are repeated 2 or more times with further transgenic host cells including at least a third, fourth, and fifth transgenic locus to obtain a stack of genetically linked transgenic loci arranged in cis.

In a particular aspect, the present invention provides a method for creating a transgenic marker-free cell including an integrated nucleic acid sequence at a selected genomic locus. In certain embodiments, the method includes transforming a host cell with at least one donor DNA construct. In particular embodiments, the donor DNA construct includes a first TALER target sequence and an exogenous DNA sequence. In other embodiments, the method includes transformation of a host cell with at least one nucleic acid sequence encoding a TALER. In one embodiment, the TALER forms part of a tetramer and mediates recombination between the first TALER target sequence and a second TALER target sequence located in the host cell genome.

In some embodiments, the method includes transformation of a host cell with at least one nucleic acid sequence encoding a selectable marker. In certain embodiments, the method includes selecting a transformed host cell expressing the selectable marker. In other embodiments, the method includes regenerating a plant from said transformed host cell, or a progeny therefrom, in the absence of selection for expression of the selectable marker. In yet other embodiments, the method includes screening the regenerated plant to confirm the absence of the selectable marker. In one embodiment, the plant includes the donor DNA construct integrated at a selected genomic locus. In one non-limiting embodiment, the method includes selecting the regenerated plant including the donor DNA construct integrated at a selected genomic locus and not containing the selectable marker.

In some embodiments, the nucleic acid sequence encoding the selectable marker is a circular molecule further including a third TALER target sequence. In certain embodiments, the TALER forms part of a tetramer and mediates recombination between the third TALER target sequence and a fourth TALER target sequence located in the host cell genome at a locus that is genetically-unlinked with the second TALER target sequence located in the host cell genome.

In particular embodiments, the donor DNA construct is linear and further includes recombinase recognition sites selected from the group consisting of Cre, FLP, phiC31, and TALER. In other embodiments, the DNA construct includes a nucleic acid sequence encoding a selectable marker. In one embodiment, the method includes transforming a host cell with a nucleic acid sequence encoding a recombinase selected from the group consisting of Cre, FLP, phiC31, and TALER. In another embodiment, the donor DNA construct is circular or linear. In yet another embodiment, the recombinase mediates recombination between the flanking recombinase recognition sites thereby excising and circularizing an intermediate sequence including the exogenous DNA sequence and the first TALER target sequence from within the nucleic acid sequence encoding the selectable marker. In still another embodiment, the excised and circularized intermediate sequence is integrated into the host cell genome by TALER-mediated recombination between the first and second TALER target sequences.

In certain embodiments, the donor DNA construct is linear and further includes viral sequences from a double-stranded DNA virus or a virus with a double-stranded DNA replication state. In particular embodiments, the DNA construct is included within the nucleic acid sequence encoding a selectable marker. In some embodiments, the viral sequences includes geminivirus or caulimovirus sequences. In one non-limiting embodiment, the method further includes transforming a host cell with a nucleic acid sequence encoding a replication protein from the virus. In still another embodiment, the replication protein mediates the formation of one or more double-stranded DNA intermediate circles including the exogenous DNA sequence and the first TALER target sequence. In other embodiment, the one or more double-stranded DNA intermediate circles are integrated into the host cell genome by TALER-mediated recombination between the first and second TALER target sequences.

In some embodiments, screening comprises PCR, DNA sequencing, or Southern blotting. In certain embodiments, the selectable marker confers antibiotic resistance or herbicide tolerance.

In an additional aspect, the present invention provides a method for generating genomic rearrangements between two selected genomic loci in a host cell. In one embodiment, the method includes transforming a host cell with at least one nucleic acid sequence encoding two sets of incompatible TALERs. In some embodiments, each TALER set forms part of a separate tetramer. In particular embodiments, the first TALER set mediates recombination between a first TALER target sequence at a first genomic locus and a second TALER target sequence at a second genomic locus. In some embodiments, the second TALER set mediates recombination between a third TALER target sequence at the first genomic locus and a fourth TALER target sequence at the second genomic locus.

In other embodiments, the method includes identifying a transformed host cell including a genomic rearrangement between two selected genomic loci in said host cell. In another embodiment, identifying a transformed host cell includes screening genomic recombination between the first genomic locus the second genomic locus in the host cell genome. In still another embodiment, the screening comprises PCR, DNA sequencing, or Southern blotting.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
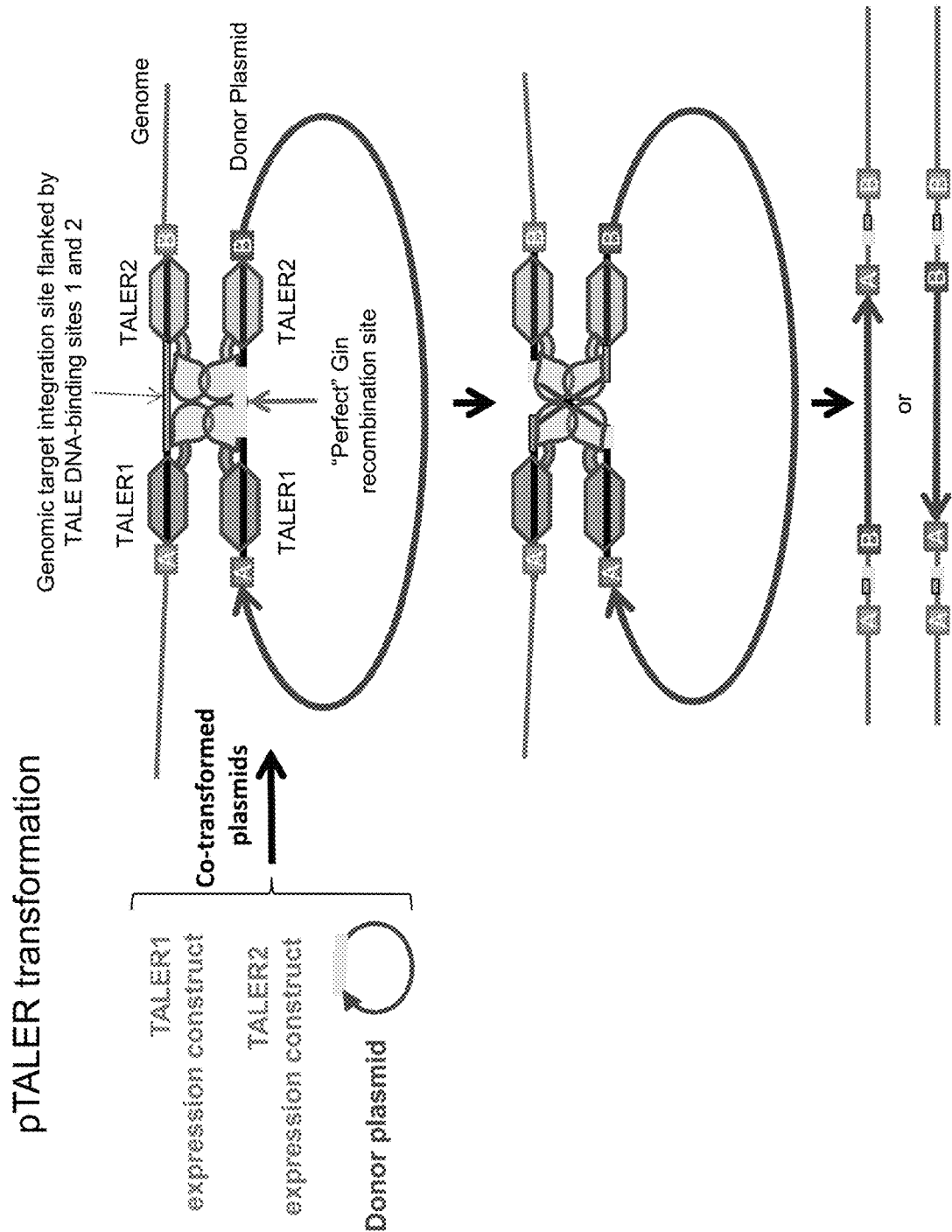
FIG. 1: A schematic representation of TALER-mediated targeted integration of exogenous DNA into a host cell genome using transformation.

The invention provides methods for the use of sequence-specific and/or sequence-directed recombinases for the modification of a target organism genome by manipulating the location and frequency of genetic recombination in a cell of the organism. For instance, the invention provides, in one embodiment, methods for using vectors and expression cassettes encoding combinations of sequences encoding TALE recombinases (TALERs). Methods for causing a TALER to modify a target genome are also provided, as are the genomic complements of an organism modified by the use of such a TALER. The invention thus provides tools and methods that allow one to insert, remove, or modify genes, loci, linkage blocks, and chromosomes within an organism.

Transcription activator-like effectors (TALEs) are DNA-binding proteins that recognize DNA in a modular fashion using a well described structural specificity thereby enabling customizable DNA targeting (Moscou and Bogdanove, 2009; Boch et al., 2009). TALE nuclease (TALEN) fusion proteins have been described that are capable of creating site-specific DNA double-strand breaks which can enable DNA sequence modifications at the break site (reviewed in Bogdanove and Voytas, 2011). Transcription activator-like effector recombinases (TALERs) are made by fusing a recombinase catalytic domain to a TALE protein. Use of fusion proteins containing DNA-binding domains and enzymatic domains is described, for example, in U.S. Patent Application Publication Nos. 2012/0222143, 2012/0214228, 2012/0192301, 2012/0178169, 2012/0178131, 2012/0110685, 2011/0301073, 2011/0239315, and 2011/0145940, which are incorporated herein by reference in their entirety.

Testing Strategies for TALERs

The invention provides novel uses for sequence-specific or sequence-directed TALERs for molecular breeding by providing a genomic nucleic acid sequence to be targeted by at least one such TALER, wherein the genomic nucleic acid sequence is native or transgenic. In addition, TALERs can be customized to catalyze recombination between one or more recognition sequences. In certain embodiments, such a custom TALER would have properties making it amenable to genetic modification such that the enzyme's recognition, binding and/or recombinase activity could be manipulated.

One aspect of this invention is to introduce into a cell a non-naturally occurring sequence-specific or sequence-directed TALER to modify the cell in such a way that the cell will subsequently confer a beneficial trait in the cell, or in an organism comprised of such cells. In one non-limiting example, the cell is a plant cell and the trait is a trait such as improved yield, quality or agronomic performance. The ability to generate such a cell, or organism derived therefrom depends on introducing the TALER using transformation vectors and cassettes described herein.

Recombinases are enzymes that catalyze DNA exchange reactions between target site nucleic acid sequences (see, e.g., Nern et al., 2011; and reviewed in Garcia-Otin and Guillou, 2006; and Turan and Bode, 2011). Examples of recombinases are well known in the art and can include, for instance, Cre recombinase (see, e.g., Nagy, 2000), Tre recombinase (see, e.g., Buchholz and Hauber, 2011), Flp recombinase (Zhu and Sadowski, 1995), Hin recombinase (see, e.g., Dhar et al., 2004).

The modular nature of many proteins, recombinases included, allow for the use of common molecular biology techniques to redesign such proteins. Native serine recombinase catalytic domains have their own target DNA sequence specificity. Recognition of a recombinase-specific DNA sequence is necessary for the enzyme to properly target its intended function. As such, contiguous fragments of some recombinases, for example small serine recombinases, have been identified which encode for the catalytic recombinase domain. However, even after the DNA-binding domain is replaced, such a recombinase retains some DNA-binding capability as required for its catalytic recombinase activity. Thus, the resulting recombination site recognized by the catalytic recombinase domain is a composite of the core catalytic DNA target sequence of the recombinase catalytic domain and any binding sites recognized by potential protein fusion partners.

Zinc finger recombinases (ZFRs) are fusions between zinc finger (ZF) DNA-binding domains and a hyperactive catalytic domain from a serine recombinase. ZFs functionally replace the native DNA-binding domain of the serine recombinase thereby changing the target sequence that the recombinase will bind and act on. Molecular evolution techniques have been used to alter the recombinase domains to change or remove their specificity. When the recombinase domain has relaxed specificity, it is able to recombine sites with different core sequences. For a recombinase domain with little or no specificity, the recombination activity would be directed to a specific sequence exclusively by the flanking ZFs.

A variable number of imperfect amino acid repeats controls TALE DNA-binding specificity (Schornack et al., 2006). Polymorphisms at repeat positions 12 and 13 (termed the repeat-variable di-residue, or RVD) directly determine which nucleotide is recognized. Various combinations of amino acid pairs located at this position correspond in a one-to-one manner (one RVD to one nucleotide) with a nucleotide targeted for binding by a TALE DNA-binding domain containing the requisite RVD (Moscou and Bogdanove, 2009; and Boch et al., 2009). As such, the TALE DNA-binding domains provided herein can recognize a specific nucleotide sequence of interest within a target DNA.

The DNA-binding domain of a TALE protein can include multiple DNA-binding repeats. Each DNA-binding repeat recognizes a single base pair within a target DNA sequence, and each DNA-binding repeat can include a RVD which is responsible for recognizing a single base pair in a target DNA sequence. RVD amino acid pair combinations that recognize a nucleotide include: histidine-aspartic acid (HD) for recognizing cytosine (C); asparagine-glycine (NG) for recognizing thymine (T); asparagine-isoleucine (NI) for recognizing adenine (A); and asparagine-asparagine (NN) for recognizing guanine (G). Additional specificities for the RVD amino acids in positions 12 and 13 and the corresponding target DNA base pair have been reported (Boch et al., 2009; and Moscou and Bogdanove, 2009).

TALERs cleave then re-ligate DNA at or near a target sequence in a target genome that exactly matches or is closely related to a specific recognition sequence. In one embodiment, the TALERs have a restricted number of recombination sites per target DNA, including, for example, a plasmid or other type of vector, or a genome. In a particular embodiment, the TALER mediates recombination at a single site in the genome. A TALER that mediates recombination between two specific recognition sequences, such that the recognition sequence is less likely to occur often within a target DNA, including but not limited to a genome, may be particularly useful. In another embodiment, the TALER-mediates recombination between two recognition sequences greater than 14 nucleic acid bases. It is recognized that the longer the recognition sequence, the less likely it is that the TALER attempt recombination more than once in the target genome.

In one embodiment, an effective TALER comprises at least the minimal portion of a TALE required for DNA-binding linked to a recombinase domain. Defining the minimal DNA-binding domain can be done empirically by making a series of truncations to a functional TALE.

In the case of TALERs with the recombinase fused to the N-terminus of the TALE, any of the many possible truncations of the C-terminus that retains robust DNA-binding activity would be acceptable and functionally equivalent. However, at the N-terminus, the truncation position can affect the positioning of the recombinase relative to the DNA-binding site. Therefore, some N-terminal truncation positions may produce TALERs with essentially equivalent DNA-binding properties but different recombination frequencies due to the intersection of TALER DNA-binding and positioning of the catalytic activity of the recombinase domain. However, in cases where attachment of the recombinase to the N-terminus of a truncated TALE does not augment TALE binding, N-terminal truncations must not be so extensive that TALE binding is impaired. In cases where attachment of the recombinase to the N-terminus of a truncated TALE does augment TALE binding, even more extensive truncations may function. Thus, experiments looking at the minimal N-terminus for TALE binding to DNA can be used to choose a range of truncation points to attach recombinases.

In particular embodiments, a TALER can include a non-permissive recombinase to mediate recombination between one or more recognition sequences. Such a specific TALER would have properties making it amenable to genetic modification such that its recognition, binding and/or recombinase activity could be manipulated.

Molecular evolution techniques have been used to alter recombinase catalytic domains to change or remove their specificity. When the recombinase domain has relaxed specificity, it is able to recombine sites with different DNA recognition sites. For a recombinase domain with little or no specificity, the recombination activity is permissive, and would be directed to a specific DNA sequence with the assistance of another DNA-binding protein. In another embodiment of the invention, a permissive recombinase is directed to a target sequence on a nucleic acid molecule by linking the recombinase to a sequence specific TALE DNA-binding protein or molecule. As an example, a TALE DNA-binding domain may be used to direct a permissive recombinase to a recognition site (i.e., "recognition sequence") within a target sequence (see, e.g., U.S. Patent Application Publication No. 2012/0110685 and 2012/0178169). Other types of catalytically active recombinases that would be suitable for use with this invention include catalytically active small serine recombinases, large serine recombinases, or tyrosine recombinases. In certain embodiments, these recombinases can have sequence specificity and built in DNA-binding activity. Ideally, a molecular breeder of, for example, plants, mushrooms, or animals, would have at his or her disposal a range of TALERs by which to induce sequence- or site-specific recombination events at, or linked to, defined sites within nucleic acid molecules or whole genomes.

In some embodiments, the recombinase catalytic domain can be tethered by an optional polypeptide linker of variable length to the N-terminus of a TALE protein (N-TALER). In other embodiments, the recombinase catalytic domain can be tethered by polypeptide linker of variable length to the C-terminus of a TALE protein (C-TALER). A unique advantage of C-TALER chimeras is that these allow for a wider selection of putative TALE targeting sequences in a host genome relative to the selection of TALE targeting sites for N-TALER chimeras. This wider selection of putative TALE targeting sites with C-TALER chimeras is due to the less restrictive orientation of TALE binding sites in a TALE targeting sequence for C-TALERs. In particular, the TALE binding site of a C-TALER monomer can be variable lengths allowing the central sequence between the two TALE binding sites to be varied. In contrast, N-TALERs have a requirement of a TALE binding site which is bounded by the first nucleotide flanking the N-TALER central sequence which should be a T or less preferably a C or even less preferably a G.

C-TALERs and N-TALERs may be used together to allow the best TALE binding sites to be selected. The flexibility provided by having the option of using N-TALERs, C-TALERs or combinations of C-TALERs and N-TALERs to choose recombination sites expands the number of possible TALER recombination sites that can be effectively used and simplifies selection of desirable sites.

The present invention also provides for use of TALER-mediated recombination to genetically alter expression and/or activity of a gene or gene product of interest in a tissue- or cell-type specific manner to improve productivity or provide another beneficial trait, wherein the nucleic acid of interest may be endogenous or transgenic in nature. Thus, in one embodiment, a TALER is engineered to mediate recombination at specific sites in a gene of interest. Genes of interest include those for which altered expression level/protein activity is desired. These recombination events can be either in coding sequences or in regulatory elements.

This invention provides for the introduction of a TALER into a cell. Exemplary TALERs include natural and engineered (i.e., modified) polypeptides with recombinase activity such as recombinases possessing sequence motifs and catalytic activities of the GinH107Y, GinL7C7-EE2, GinL7C7-EE3, HinB(HinH106Y), and HinC variants (see Gordley et al., 2009; Gersbach et al., 2010; and Gordley et al., 2007), as well as small serine recombinases, large serine recombinases, and tyrosine recombinases, naturally occurring or engineered for a given target specificity. Contemplated recombinases include the Cre recombinase (see, e.g., Nagy, 2000), the Tre recombinase (see, e.g., Buchholz and Hauber, 2011), the Flp recombinase (Zhu and Sadowski, 1995), the Hin recombinase (see, e.g., Johnson, 2004), and those recombinases known in the art.

To be effective, the catalytically active TALER must be introduced to, or produced by, a target cell. The present invention contemplates multiple strategies for delivery and expression of TALERs to cells.

Transient Expression of TALERs

In some embodiments, the TALER is transiently introduced into the cell. In certain embodiments, the introduced TALER is provided in sufficient quantity to modify the cell but does not persist after a contemplated period of time has passed or after one or more cell divisions. In such embodiments, no further steps are needed to remove or segregate the TALER from the modified cell.

In another embodiment, mRNA encoding the TALER is introduced into a cell. In such embodiments, the mRNA is translated to produce the TALER in sufficient quantity to modify the cell but does not persist after a contemplated period of time has passed or after one or more cell divisions. In such embodiments, no further steps are needed to remove or segregate the TALER from the modified cell.

In one embodiment of this invention, a catalytically active TALER is prepared in vitro prior to introduction to a cell, including a prokaryotic or eukaryotic cell. The method of preparing a TALER depends on its type and properties and would be known by one of skill in the art. For example, if the TALER is a chimeric recombinase with a catalytically active small serine recombinase domain, the active form of the TALER can be produced via bacterial expression, in vitro translation, via yeast cells, in insect cells, or by other protein production techniques described in the art. After expression, the TALER is isolated, refolded if needed, purified and optionally treated to remove any purification tags, such as a His-tag. Once crude, partially purified, or more completely purified TALERs are obtained, the TALER may be introduced to, for example, a plant cell via electroporation, by bombardment with TALER coated particles, by chemical transfection or by some other means of transport across a cell membrane. Methods for introducing nucleic acids into bacterial and animal cells are similarly well known in the art. The protein can also be delivered using nanoparticles, which can deliver a combination of active protein and nucleic acid (Torney et al., 2007). Once a sufficient quantity of the TALER is introduced so that an effective amount of in vivo recombinase activity is present, the target site or sites are looped out. It is also recognized that one skilled in the art might create a TALER that is inactive but is activated in vivo by native processing machinery; such a TALER is also contemplated by this invention.

In another embodiment, a construct that will transiently express a TALER is created and introduced into a cell. In yet another embodiment, the vector will produce sufficient quantities of the TALER in order for the desired target site or sites to be effectively recombined. For instance, the invention contemplates preparation of a vector that can be bombarded, electroporated, chemically transfected or transported by some other means across the plant cell membrane. Such a vector could have several useful properties. For instance, in one embodiment, the vector can replicate in a bacterial host such that the vector can be produced and purified in sufficient quantities for a transient expression. In another embodiment, the vector can encode a drug resistance gene to allow selection for the vector in a host, or the vector can also comprise an expression cassette to provide for the expression of the TALER in an organism. In a further embodiment, the expression cassette could contain a promoter region, a 5' untranslated region, an optional intron to aid expression, a multiple cloning site to allow facile introduction of a sequence encoding a TALER, and a 3' UTR. In some embodiments, it can be beneficial to include unique restriction sites at one or at each end of the expression cassette to allow the production and isolation of a linear expression cassette, which can then be free of other vector elements. The untranslated leader regions, in certain embodiments, can be plant-derived untranslated regions. Use of an intron, which can be plant-derived, is contemplated when the expression cassette is being transformed or transfected into a monocot cell.

In other embodiments, one or more elements in the vector include a TALER target sequence. This facilitates recombination within the expression cassette, enabling removal and/or insertion of elements such as promoters and transgenes. Use of recombination to modify or delete transgenes is described, for example, in International Publication Nos. WO2001066780A3, WO2001066780A2, U.S. Patent Application Publication Nos. 2008/0178348, 2005/0060769, 2001/0056583, and U.S. Pat. Nos. 6,750,379, and 6,580,019, which are incorporated herein by reference in their entirety.

In another approach, a transient expression vector may be introduced into a cell using a bacterial or viral vector host. For example, *Agrobacterium* is one such bacterial vector that can be used to introduce a transient expression vector into a host cell. When using a bacterial, viral or other vector host system, the transient expression vector is contained within the host vector system. For example, if the *Agrobacterium* host system is used, the transient expression cassette would be flanked by one or more T-DNA borders and cloned into a binary vector. Many such vector systems have been identified in the art (reviewed in Hellens et al., 2000).

In embodiments whereby the TALER is transiently introduced in sufficient quantities to modify a cell, a method of selecting the modified cell may be employed. In one such method, a second nucleic acid molecule containing a selectable marker is co-introduced with the transient TALER. In this embodiment, the co-introduced marker may be part of a molecular strategy to introduce the marker at a target site. For example, the co-introduced marker may be used to disrupt a target gene by inserting between recombination sites. In another embodiment, the co-introduced nucleic acid may be used to produce a visual marker protein such that transfected cells can be cell-sorted or isolated by some other means. In yet another embodiment, the co-introduced marker may randomly integrate or be directed via a second TALER to integrate at a site independent of the primary target site. In still yet another embodiment, the co-introduced molecule may be targeted to a specific locus via recombination between recognition sites of the TALER. In the above embodiments, the co-introduced marker may be used to identify or select for cells that have likely been exposed to the TALER and therefore are likely to have been modified by the TALER.

Stable Expression of TALERs

In another embodiment, a circular TALER vector is stably transformed into a cell so as to bind a recognition sequence at or near the target site in the host genome with a TALE DNA-binding domain as well as a recognition sequence within the vector, and the recombinase domain recombines the two recognition sequences thereby integrating the circular vector into the genome. In this embodiment, the design of the transformation vector provides flexibility for when and under what conditions the TALER is expressed. Furthermore, the transformation vector can be designed to comprise a selectable or visible marker that will provide a means to isolate or efficiently select cell lines that contain and/or have been modified by the TALER. In a certain embodiment, a linear TALER vector is stably transformed into a cell so as to bind two recognition sequences within the vector with a TALE DNA-binding domain, wherein the recombinase domain recombines the two plasmid recognition sequences thereby circularizing the vector, after which the TALE DNA-binding domain of the TALER binds a recognition sequence at or near the target site in the host genome as well as the recognition sequence within the newly formed circular TALER vector, and the recombinase domain recombines the two recognition sequences thereby integrating the newly formed circular vector into the genome.

Cell transformation systems have been described in the art and descriptions include a variety of transformation vectors. For example, for plant transformations, two principal methods include *Agrobacterium*-mediated transformation and particle gun bombardment-mediated (i.e., biolistic) transformation. In both cases, the TALER is introduced via an expression cassette. The cassette may contain one or more of the following elements: a promoter element that can be used to express the TALER; a 5' untranslated region to enhance expression; an intron element to further enhance expression in certain cell types, such as monocot cells; a multiple-cloning site to provide convenient restriction sites for inserting the TALER-encoding sequence and other desired elements; and a 3' untranslated region to provide for efficient termination of the expressed transcript. For particle bombardment or with protoplast transformation, the expression cassette can be an isolated linear fragment or may be part of a larger construct that might contain bacterial replication elements, bacterial selectable markers or other elements. The TALER expression cassette may be physically linked to a marker cassette or may be mixed with a second nucleic acid molecule encoding a marker cassette. The marker cassette is comprised of necessary elements to express a visual or selectable marker that allows for efficient selection of transformed cells. In the case of *Agrobacterium*-mediated transformation, the expression cassette may be adjacent to or between flanking T-DNA borders and contained within a binary vector. In another embodiment, the expression cassette may be outside of the T-DNA. The presence of the expression cassette in a cell may be manipulated by positive or negative selection regime(s). Furthermore, a selectable marker cassette may also be within or adjacent to the same T-DNA borders or may be somewhere else within a second T-DNA on the binary vector (e.g., a 2 T-DNA system).

In another embodiment, cells that have been modified by a TALER, either transiently or stably, are carried forward along with unmodified cells. The cells can be sub-divided into independent clonally derived lines or can be used to regenerate independently derived organisms. Individual plants or animals or clonal populations regenerated from such cells can be used to generate independently derived lines. At any of these stages a molecular assay can be employed to screen for cells, organisms or lines that have been modified. Cells, organisms or lines that have been modified continue to be propagated and unmodified cells, organisms or lines are discarded. In these embodiments, the presence of an active TALER in a cell is essential to ensure the efficiency of the overall process.

Expression Strategies for TALERs

Promoters for transformation have been described in the art; thus the invention provides, in certain embodiments, novel combinations of promoters and a sequence encoding a TALER, to allow for specifically introducing a recombination event into endogenous DNA (i.e., a genome). In one embodiment, a constitutive promoter is cloned 5' to a TALER-encoding gene, in order to constitutively express the TALER in transformed cells. This may be desirable when the activity of the TALER is low or the frequency of finding and recombining the target site is low. It may also be desirable when a promoter for a specific cell type, such as the germ line, is not known for a given species of interest.

In another embodiment, an inducible promoter can be used to turn on expression of the TALER under certain conditions. For example, a cold shock promoter cloned upstream of a TALER might be used to induce the TALER under cold temperatures. Other environmentally inducible promoters have been described and can be used in a novel combination with a TALER-encoding sequence. Another type of inducible promoter is a chemically inducible promoter. Such promoters can be precisely activated by the application of a chemical inducer. Examples of chemical inducible promoters include the steroid inducible promoter and a quorum sensing promoter (see, e.g., You et al., 2006; U.S. Patent Application Publication No. 2005/0227285). Recently it has been shown that modified RNA molecules comprising a ligand specific aptamer and riboswitch can be used to chemically regulate the expression of a target gene (Tucker et al, 2005; International Publication No. WO2006073727). Such a riboregulator can be used to control the expression of a TALER-encoding gene by the addition or elimination of a chemical ligand.

In other embodiments, the promoter is a tissue specific promoter, a developmentally regulated promoter, or a cell cycle regulated promoter. Certain contemplated promoters include ones that only express in the germline or reproductive cells, among others. Such developmentally regulated promoters have the advantage of limiting the expression of the TALER to only those cells in which DNA is inherited in subsequent generations. Therefore, a TALER-mediated genetic modification (i.e., genetic recombination) is limited only to cells that are involved in transmitting their genome from one generation to the next. This might be useful if broader expression of the TALER were genotoxic or had other unwanted effects.

Another contemplated promoter is a promoter that directs developmentally regulated expression limited to reproductive cells just before or during meiosis. Such a promoter has the advantage of expressing the TALER only in cells that have the potential to pass on their genome to a subsequent generation. Examples of such promoters include the promoters of genes encoding DNA ligases, recombinases, replicases, and so on.

Tissue- and development-specific promoters are additionally useful to control gamete development and essentially create haploid material (akin to haploid induction in a double haploid (DH) plant). Another aspect of this technology that is parallel to maternal induction systems in a DH comprises use of a pollen expressed TALER that can recombine in one or more sites in the male gamete genome to disable fertilization. Conveniently, the resulting seed would thus not contain a gene product. Resulting haploid cells, haploid embryos, haploid seeds, haploid seedlings, or haploid plants can be chemically treated with a doubling agent. Non-limiting examples of known doubling agents include nitrous oxide gas, anti-microtubule herbicides, anti-microtubule agents, colchicine, pronamide, and mitotic inhibitors.

Other tissue/development specific control mechanisms include manipulating pollen delay by targeting pollen development pathway elements or cytoplasmic male sterility elements to generate male sterile plants, which has utility for eliminating manual pollination practices in breeding and manufacturing hybrid crops.

In another embodiment, the promoter can be part of a two component system and can be activated when a second component is provided. For example, the promoter may require a non-native transcription factor to bind and activate. This transcription factor may be provided by crossing to a line expressing the second component. In a further elaboration, the second component may be regulated in an environmental, tissue or developmental specific manner.

In addition to promoters, this invention provides for 5' untranslated regions, introns and 3' untranslated regions that can be uniquely combined with a TALER-encoding sequence to create novel expression cassettes with utility for genome engineering.

Transformation Methods

Methods for transforming or transfecting a cell are well known in the art. Methods for plant transformation using *Agrobacterium* or DNA coated particles are well known in the art and are incorporated herein. Suitable methods for transformation of host cells for use with the current invention are believed to include virtually any method by which DNA can be introduced into a cell (see, e.g., Miki et al., 1993), for example by *Agrobacterium*-mediated transformation (U.S. Pat. Nos. 5,563,055; 5,591,616; 5,693,512; 5,824,877; 5,981,840; 6,384,301; Gelvin, 2003; and Broothaerts et al., 2005) and by acceleration of DNA coated particles (U.S. Pat. Nos. 5,015,580; 5,550,318; 5,538,880; 6,160,208; 6,399,861; and 6,403,865), etc. Through the application of techniques such as these, the cells of virtually any species may be stably transformed.

Various methods for selecting transformed cells have been described. For example, one might utilize a drug resistance marker such as a neomycin phosphotransferase protein to confer resistance to kanamycin or to use 5-enolpyruvyl shikimate phosphate synthase to confer tolerance to glyphosate. In another embodiment, a carotenoid synthase is used to create an orange pigment that can be visually identified. These three exemplary approaches can each be used effectively to isolate a cell or multicellular organism or tissue thereof that has been transformed and/or modified by a TALER.

When a nucleic acid sequence encoding a selectable or screenable marker is inserted into a genome at the same locus as a TALER-encoding sequence or TALER target sequence, the marker can be used to detect the presence or absence of the TALER or its activity. This may be useful once a cell has been modified by the TALER, and recovery is desired of a genetically modified cell, or a regenerated organism from such a modified cell, that no longer contains the TALER. In other embodiments, the marker may be intentionally designed to integrate at the recombination site, such that it can be used to follow a modified cell independent of the TALER. The marker can be a gene that provides a visually detectable phenotype, such as in the seed, to allow rapid identification of seeds that carry or lack the TALER gene.

This invention provides for a means to regenerate an organism from a cell with a stably integrated sequence-directed recombinase. The regenerant can then be used to propagate additional organisms.

The invention additionally provides novel plant transformation vectors and expression cassettes which include novel combinations of a TALER with expression and transformation elements. The invention further provides methods of obtaining a cell, a whole plant or animal, and a seed or embryo that have been specifically modified using a TALER. This invention also relates to a novel cell or organism containing a non-naturally occurring sequence-specific or sequence-directed TALER.

Detection of Recombinase Activity and TALER-Mediated Genomic Modification in Cells The invention also provides molecular assays for detecting and characterizing cells that have been modified by a TALER. These assays include but are not limited to genotyping reactions, a PCR assay, a sequencing reaction or other molecular assay. Design and synthesis of nucleic acid primers useful for such assays, for instance to assay for the occurrence of a recombination event, are also contemplated.

Genotyping can be utilized, for instance by high throughput, non-destructive seed sampling for one or more markers, such as genetic markers. This sampling approach permits the rapid identification of seed comprising preferred or selected genotypes or phenotypic characters such that only preferred or targeted seed is planted, saving resources on greenhouse and/or field plots. Apparatus and methods for the high throughput, non-destructive sampling of seeds have been described. For example, U.S. Patent Application Publication Nos. 2006/0048247; 2006/0048248; 2006/0042527; 2006/0046244; 2006/0046264; and 2007/0204366; which are incorporated herein by reference in their entirety, disclose apparatus and systems for the automated sampling of seeds as well as methods of sampling, testing and bulking seeds.

Use of Custom TALERs in Molecular Breeding

In some embodiments, genome knowledge is utilized for targeted genetic alteration of a genome. At least one custom TALER can be designed to target at least one region of a genome to delete that region from the genome. This aspect of the invention may be especially useful for genetic alterations. The resulting organism could have a modified phenotype or other property depending on the gene or genes that have been removed. Previously characterized mutant alleles or introduced transgenes can be targeted for TALER re-design, enabling creation of improved mutants or transgenic lines.

In another embodiment, a gene targeted for deletion or disruption may be a transgene that was previously introduced into the target organism or cell. This has the advantage of allowing an improved version of a transgene to be introduced or by allowing removal of a selectable marker encoding sequence. In yet another embodiment, a gene targeted for deletion or disruption via recombination is at least one transgene that was introduced on the same vector or expression cassette as (an)other transgene(s) of interest, and resides at the same locus as another transgene. It is understood by those skilled in the art that this type of recombination may result in deletion or insertion of additional sequences. Thus it may, in certain embodiments, be preferable to generate a plurality of organisms or cells in which a deletion has occurred, and to screen such organisms or cells using standard techniques to identify specific organisms or cells that have minimal alterations in their genomes following recombination. Such screens may utilize genotypic and/or phenotypic information. In such embodiments, a specific transgene may be removed while leaving the remaining transgene(s) intact. This avoids having to create a new transgenic line containing the desired transgenes without the undesired transgene.

In another aspect, the present invention includes methods for inserting a nucleic acid of interest into a specific site of an organism's genome, wherein the nucleic acid of interest is from the genome of the organism or is heterologous with respect to the organism. This invention allows one to select or target a particular region of the genome for nucleic acid (i.e., transgene) stacking (i.e., mega-locus). A targeted region of the genome may thus display linkage of at least one transgene to a haplotype of interest associated with at least one phenotypic trait, and may also result in the development of a linkage block to facilitate transgene stacking and transgenic trait integration, and/or development of a linkage block while also allowing for conventional trait integration. In another embodiment of this invention, a pair of sequence specific TALERs may be used to move a sequence specifying an allele contained on a specific locus within one linkage block contained on one chromosome to the same locus within a different linkage block on the homologous chromosome. Progeny containing the transferred allele in the new linkage context may exhibit one or more different traits, depending on the transferred allele and the alleles on the new linkage block.

For instance, a TALER that is specific for, or can be directed to, a recognition sequence that is upstream of the locus containing the non-target allele is selected. A second TALER that is specific for, or can be directed to, a recognition sequence that is downstream of the target locus containing the non-target allele may also be selected. The TALERs can be selected such that they recombine in regions where there is no homology to the non-target locus containing the target allele. Both TALERs are cloned into expression cassettes and introduced into a cell using one of the methods described above. Once introduced, the TALERs are expressed based on the properties of the promoter and other regulatory elements found in each expression cassette that comprises a TALER-encoding sequence. The TALERs can then be expressed, and can recombine upstream and downstream of the target locus, respectively.

The suitable distance between TALE binding sites for a particular TALER target sequence will vary depending on the TALER architecture used. In certain embodiments, the distance between the TALE binding sites for a particular TALER target sequence (binding sites begin with the 5' T and end with the last nucleotide contacted by a TALE RVD repeat) can be 18 to 50 bp. In other embodiments, the distance can be 18, 20 or 40 bp. In yet other embodiments, the distance can be from about 18 bp to about 50 bp.

In some embodiments, TALER target sequences with a preferred di-nucleotide at or near the center of the TALER central sequence between the TALE binding sites can be chosen. In particular embodiments, the di-nucleotides are AT, AA, TT, TC or GA. In other embodiments, the di-nucleotides are AT, AA and TT.

Use of TALERs in Trait Integration

Directed insertion via custom TALERs for at least one recognition sequence in the genome, allows for targeted insertion of multiple nucleic acids of interest (i.e., a trait stack or mega-locus) to be added to the genome of a plant or animal, in either the same site or different sites. Sites for targeted integration can be selected based on knowledge of the underlying breeding value, transgene performance in that location, underlying recombination rate in that location, existing transgenes in that linkage block, or other factors.

Once the stacked organism is assembled, it can be used as a trait donor for crosses to germplasm being advanced in a breeding pipeline or be directly advanced in the breeding pipeline.

The present invention includes methods for inserting at least one nucleic acid of interest into at least one site, wherein the nucleic acid of interest is from the genome of an organism, such as a QTL or allele, or is transgenic in origin. A targeted region of the genome may thus display linkage of at least one transgene to a haplotype of interest associated with at least one phenotypic trait (as described in U.S. Patent Application Publication No. 2006/0282911), development of a linkage block to facilitate transgene stacking and transgenic trait integration, development of a linkage block to facilitate QTL or haplotype stacking and conventional trait integration, and so on.

In another embodiment of this invention, a pair of sequence-specific TALERs can be used to move an allele at a specific locus within one linkage block contained on one chromosome to the same locus within a different linkage block on the homologous chromosome by making use of knowledge of genomic sequence information and the ability to design custom TALER TALE DNA-binding domains as described in the art. A TALE DNA-binding domain that is specific for, or can be directed to, a recognition sequence that is upstream of the locus containing the non-target allele is selected from a library of TALE DNA-binding domains or engineered as necessary. A second TALE DNA-binding that is specific for, or can be directed to, a recognition sequence that is downstream of the target locus containing the non-target allele is also selected or engineered. The TALERs may be selected such that they bind in regions where there is no homology to the non-target locus containing the target allele. Both TALERs may be introduced into a cell using one of the methods described above.

In another aspect, this technology enables the identification of the one or more loci in a genome to be used for transgene insertion. Site-directed integration allows the comparison of one or more transgenes inserted in the same position across multiple germplasm as well as comparison of different expression elements in a transgenic construct. For example, 10, 100, 1000, 10,000 or 100,000 custom TALERs can be generated and used for target integration of at least one construct. The recognition sequence for a TALER can be artificially introduced into the genome and resulting events can be screened or multiple custom TALE DNA-binding domains for corresponding unique recognition sequences can be generated.

At least one expression construct encoding at least one nucleic acid of interest may be evaluated for position effects to determine a preferred location for integration of sequences of that construct, thus allowing for enhanced breeding efficiency, including more efficient trait integration than the current state of the art that typically relies on random integration, and thus does not allow for such controlled testing and comparison. In addition, by being able to target a given insertion site or locus of interest, variations of a given recombinant construct designed to insert into or otherwise manipulate genomic nucleic acid sequence at the locus of interest, and for instance comprising alternate genetic regulatory elements such as an alternate promoter or terminator, may then be tested at the given locus. The described methods thus further allow for the above multivariate experiments to be conducted across germplasm, wherein position effects, promoter effects, and so on are tested in at least two different germplasm entries. Custom TALERs allow testing for the identification of identified insertion sites for the performance of one or more transgenes. Methods and compositions relating to breeding for improved transgene performance are provided in U.S. Patent Application Publication No. 2009/2481438, which is incorporated herein by reference. Custom TALERs enable experiments to compare different insertion sites as well as different construct design at the same insertion site, further facilitating development of germplasm-transgene combinations for enhanced transgene performance.

Further, as described herein, this process can be conducted simultaneously or serially with manipulation of the DNA repair/recombination pathways to increase the efficiency of targeted insertion.

The ability to execute targeted integration relies on the action of the TALE DNA-binding domain and the recombinase domain of the TALER. This advantage provides methods for engineering organisms of interest, including a plant or animal or a cell, comprising at least one genomic modification.

The present invention also contemplates that one or more genetic elements involved in DNA repair, recombination, or meiosis may be manipulated using gene suppression, transgenic expression constructs, and/or at least one other TALER to target the genetic element. This strategy can direct the outcome of the TALER-induced recombination event to favor targeted integration or deletion. Once the action of the TALER has occurred, the result is a non-naturally occurring modified cell. Organisms derived from and/or containing this cell can thus display a trait of interest, such as enhanced yield, quality or agronomic performance.

In the course of using TALERs to target insertion to specific sequences, coupling targeted integration with recombination control permits the rapid generation of inbreds, eliminating the need for selfing or recurrent selection. The methods of this invention also enables trait integration on segregating material, saving time and resources in a breeding program and enabling rapid development of sister lines. Steps may include, but are not limited to, the use of a positive-negative selection system (Lida et al., 2004) or suppression of certain pathway genes. Methods for overexpression or suppression are known to those skilled in the art.

In another aspect, the present invention provides methods for controlling the rate of recombination in the genome of a crop plant. In one embodiment, recombination rate for at least one genomic region of interest is increased in order to increase the number of potential recombinants at the genomic region.

In another embodiment, recombination is inhibited thus fixing the genome of an organism in one step. In a particular embodiment, recombination is inhibited after targeted insertion of one or more nucleic acids of interest, as enabled by an engineered TALER (i.e., a custom TALE DNA-binding domain fused to a recombinase). This can be accomplished, for instance, by co-transformation or by achieving directed recombination via action of a TALER, and subsequently by administration of recombination and/or meiosis inhibition agents, such as a transgenic approach based on manipulation of a gene involved in meiosis or DNA repair. This combination of technologies provides a strategy for "instant" trait integration.

This present invention combines tools for site-directed gene integration as well as manipulation of recombination rate (i.e., inhibition or enhancement), for instance enabling rapid trait integration wherein recombination is inhibited by suppression or elimination of one or more elements of meiosis or by using approaches, such as production of a dihaploid, to rapidly generate an inbred or homozygous line displaying a trait of interest. Trait integration, especially for two or more traits, is time consuming and resource intensive. The present invention advances the state of the art of transgenic breeding by combining methods for recombination inhibition with methods for directed recombination, i.e., targeted gene integration.

A custom TALER can be utilized to generate at least one trait donor to create a custom transgenic event that is then crossed into at least one second organism of interest, including a plant or animal, wherein TALER delivery can be coupled with the nucleic acid of interest to be inserted. In other aspects one or more organisms of interest are directly transformed with the TALER and at least one nucleic acid of interest for directed insertion. It is recognized that this method may be executed in various cell, tissue, and developmental types, including gametes. It is further anticipated that one or more of the elements described herein may be combined with use of promoters specific to particular cells, tissues, organs and/or development stages, such as a meiosis-specific promoter.

In certain aspects, the TALER and recombination inhibition elements are delivered simultaneously though not necessarily expressed simultaneously. Alternatively, the site-directed integration and recombination inhibition elements are delivered separately. In addition, any of the steps described above may be carried out at any stage of development, including gametes, embryos, cell culture, other tissues, and organisms. In certain aspects, cells are provided that have been modified to confer an improved trait. Taken together, the invention enables a plant or animal breeder to use new tools and efficiencies for manipulating a genome within a germplasm pool.

In addition, the invention contemplates the targeting of a transgenic element already existing within a genome for deletion or disruption. This allows, for instance, an improved version of a transgene to be introduced, or allows selectable marker removal. In yet another embodiment, a gene targeted for deletion or disruption via recombination is at least one transgene that was introduced on the same vector or expression cassette as (an)other transgene(s) of interest, and resides at the same locus as another transgene. In one embodiment, the transgene(s) can be deleted through the action of TALERs, as described above, independent of homologous recombination pathways.

In one aspect, the invention thus provides a method for modifying a locus of interest in a cell comprising (a) identifying at least one locus of interest within a DNA sequence; (b) creating a modified nucleotide sequence, in or proximal to the locus of interest, that includes a recognition sequence for a first recombinase according to the invention; (c) introducing into at least one cell the recombinase, wherein the recombinase is expressed transiently or stably; (d) assaying the cell for a recombinase-mediated modification in the DNA making up or flanking the locus of interest; and (e) identifying the cell or a progeny cell thereof as comprising a modification in said locus of interest.

Further provided is a method for modifying a locus of interest in a cell comprising (a) identifying at least one locus of interest within a DNA sequence; (b) creating a modified nucleotide sequence at the locus of interest, in or proximal to the locus of interest, that includes a recognition sequence for a first chimeric recombinase according to the invention; (c) introducing into at least one cell the chimeric recombinase, wherein the chimeric recombinase is expressed transiently or stably; (d) assaying the cell for a modification caused by the chimeric recombinase in the DNA sequence making up or flanking the locus of interest; and (e) identifying a cell or a progeny cell thereof as comprising a modification in said locus of interest.

A third aspect provides a method for modifying a locus of interest in a cell comprising (a) identifying at least one locus of interest within a DNA sequence; (b) identifying at least one chimeric recombinase recognition sequence within the locus of interest; (c) introducing into at least one cell at least one chimeric recombinase according to the invention, wherein the cell comprises the recognition sequence in or proximal to the locus of interest and the chimeric recombinase is expressed transiently or stably and creates modified site that includes at least one recognition sequence for the chimeric recombinase; (d) assaying the cell for a chimeric recombinase-mediated modification in the DNA making up or flanking the locus of interest; (e) identifying a cell or a progeny cell thereof which comprises a modified nucleotide sequence at said locus of interest and (f) introducing into the identified cell at least another chimeric recombinase which recognizes the modified nucleotide sequence at the locus of interest.

The invention further provides a method comprising one or more steps subsequent to step (f), wherein the locus which comprises the sequence recognized by this other chimeric recombinase is further modified. Thus sequential modification of a locus of interest, by two or more chimeric recombinase according to the invention, is contemplated, and genes or other sequences added by the action of such a first chimeric recombinase may be retained, further modified, or removed by the action of a second chimeric recombinase. Sequences, including modified sequences, at a locus of interest may also be modified or removed, or alternatively retained, during subsequent breeding or other crop development activities, for instance with or without further use of a chimeric recombinase.

Definitions

The definitions and methods provided define the present invention and guide those of ordinary skill in the art in the practice of the present invention. Unless otherwise noted, terms are to be understood according to conventional usage by those of ordinary skill in the relevant art. Definitions of common terms in molecular biology may also be found in Alberts et al., Molecular Biology of The Cell, 5th Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2247; and Lewin, Genes IX, Oxford University Press: New York, 2007. The nomenclature for DNA bases as set forth at 37 CFR § 1.822 is used.

As used herein, "domain" refers to a polypeptide that includes an amino acid sequence of an entire polypeptide or a functional portion of a polypeptide. Certain functional subsequences are known, and if they are not known, can be determined by truncating a known sequence and determining whether the truncated sequence yields a functional polypeptide.

As used herein, "TALE protein" refers to a transcription activator-like effector (TALE) protein originally identified as a virulence factor from the phytopathogenic bacterial genus *Xanthomonas* or *Ralstonia*. TALE proteins bind DNA in the nucleus, via a domain of DNA-binding repeats, where they act as transcriptional activators thereby contributing to virulence.

As used herein, "TALER site" or "TALER recombination site" refers to a sequence that comprises a TALER central sequence and can be recombined by a TALER or a set of TALERs.

As used herein, "TALE DNA-binding domain" refers to the domain of a TALE protein, or chimeric TALE-recombinase (TALER) protein, that binds to a specific DNA sequence, defined herein as a "TALE binding site" (TBS), via a domain of DNA-binding repeats. As used herein, "DNA-binding repeat" refers to a sequence containing a variable number (typically 34) of amino acids, typically found in the context of an imperfectly-repeating set. Each DNA-binding repeat can include hypervariable amino acid residues, defined herein as "repeat-variable di-residues" (RVDs), typically at positions 12 and 13.

As used herein, "TALER" refers to a chimeric protein which combines at least a first hyperactive recombinase catalytic domain from a recombinase tethered, by an optional polypeptide linker of variable length, to the N- or C-terminus of a TALE protein.

As used herein, "recombinase core sequence" is defined as the recombination-site DNA sequence minimally required for recognition as a substrate for a recombinase catalytic domain. As used herein, "TALER target sequence" refers to a nucleic acid sequence encoding a TALE binding site followed by an optional spacer followed by a recombinase core sequence followed a spacer sequence followed by a TALE binding site.

As used herein, "TALER central sequence" refers to a nucleic acid sequence flanked by TALER binding sites. In some embodiments, the TALER central sequence contains a recombinase core sequence with flanking, adjoining, optional spacer. In other embodiments, the TALER central sequence of one TALER site does not contain a core sequence but can be recombined with a second TALER site that does contain a core sequence. As used herein, "TALER expression construct" refers to a DNA construct that includes an encoded chimeric TALER protein that can be transcribed.

As used herein, "TALER reporter construct" refers to a DNA construct that includes synthetic TALER target sequences where two TALE binding sites, flanking a recombinase core sequence, are oriented such that the recombinase domains of the TALER proteins, when bound to the DNA, will be positioned at the recombinase core sequence between the two TALE binding sites (Table 1). In certain embodiments, the TALER reporter constructs described herein include a recombinase core sequence, that is recombined by the native Gin recombinase, and a 5' and 3' spacer sequence (Table 1).

As used herein, "spacer" refers to a nucleotide sequence between a TALE binding site and a recombinase core sequence (Table 1).

As used herein, "linker" refers to an amino acid sequence tethering the recombinase catalytic domain to the TALE protein.

As used herein, "perfect Gin recombinase sequence" or refers to a recombinase core sequence that is efficiently recombined with itself by a permissive or stringent, hyperactive Gin recombinase. As used herein, "native Gin recombinase sequence" refers to all or part of the sequence that is the natural target of recombination of the Gin recombinase or a variant of that sequence where the central dinucleotide site of recombination is AT, AA, or TT.

As used herein, "exogenous DNA sequence" refers to DNA that is produced outside a cell. The sequence of such DNA may be obtained from a different species (i.e., transgenes) or the same species (i.e., cis genes) as the species of the cell into which it is being delivered.

A palindromic sequence is a nucleic acid sequence that is the same whether read 5' to 3' on one strand or 3' to 5' on the complementary strand with which it forms a double helix. A nucleotide sequence is said to be a palindrome if it is equal to its reverse complement. A palindromic sequence can form a hairpin. Thus, as used herein, a "pseudo-palindrome sequence" refers to an imperfect palindromic sequence wherein not all the nucleic acid base pairs obey a hairpin two-fold symmetry.

As used herein, a "selectable marker" refers to a sequence or gene cassette that facilitates the recovery of a transformed cell.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Figure 2:
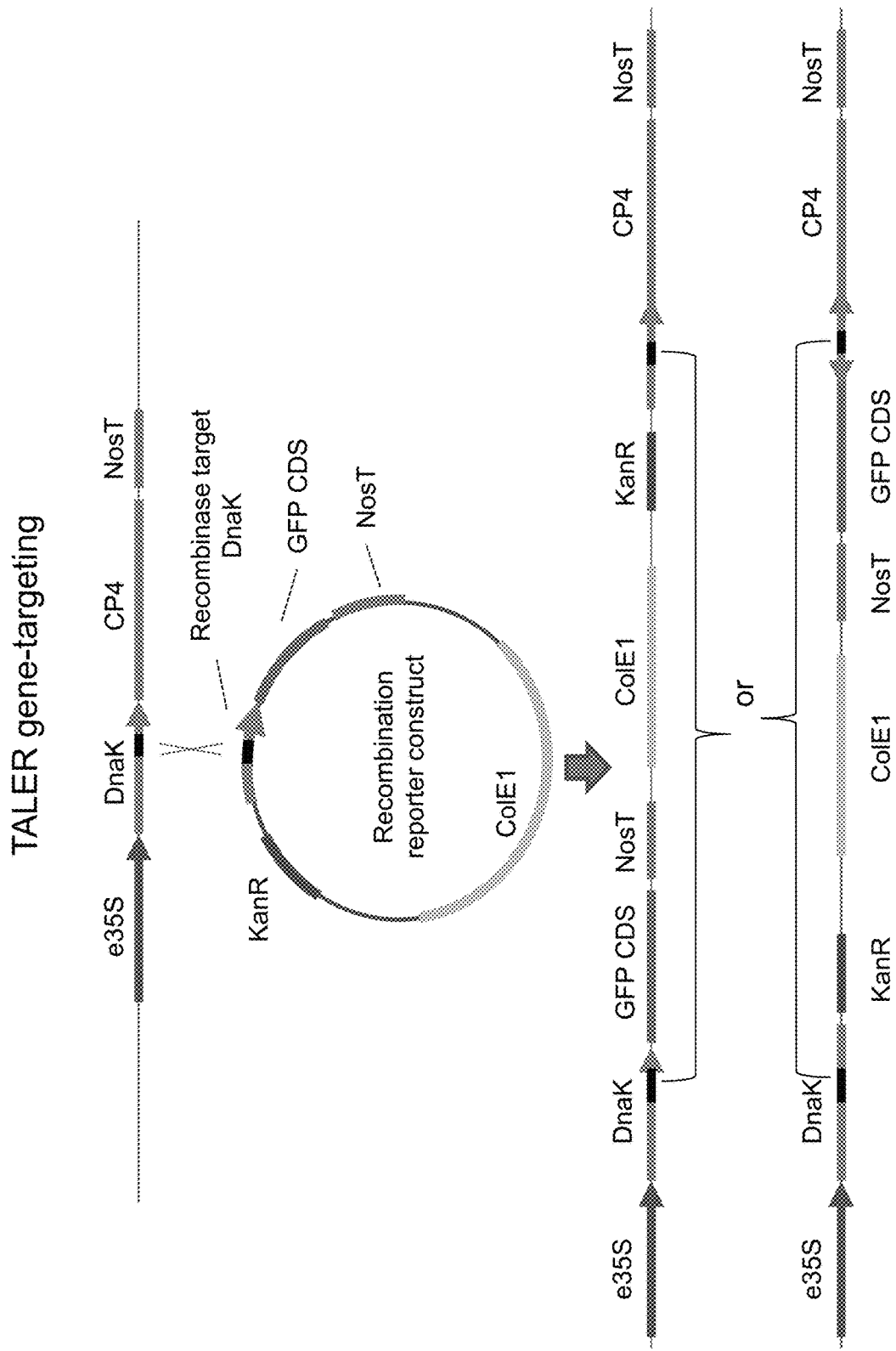
FIG. 2: A schematic representation of TALER-mediated gene-targeting in a pMON58401 transgenic corn line.

TALER-Mediated Targeted Integration of Exogenous DNA into a Specified Host Genomic Locus DNA constructs have been designed to integrate, by TALER-mediated recombination, a green fluorescent protein (GFP) coding sequence (CDS) downstream from a strong constitutive promoter (e35S) driving expression of a CP4-EPSPS CDS in a corn transgenic line. Correctly targeted events would result in e35S-driven GFP expression and detectable fluorescence (FIG. 2). Because TALER-mediated integration will not be directional, correctly targeted GFP integration events with improper CDS orientation, and thus no GFP expression, are expected. Transformants can be screened, by PCR or other techniques, to identify random integration events resulting in GFP expression.

Four target insertion sites (TR1, TR2, TR3, and TR6) have been chosen in the transgenic corn genome; three sites (TR1, TR2, and TR3) inside the integrated CP4-EPSPS cassette, and one site (TR6) at a separate locus outside of the integrated CP4-EPSPS cassette. Sites TR1 and TR2 target two separate sites within the DnaK intron. Site TR3 targets within the CP4-EPSPS CDS. Site TR6 targets a separate corn genomic locus, the Zm5.1 site. TALER-mediated recombination at TR6 will use an NptII CDS, and paromycin selection of transformants, instead of a GFP CDS. For each target integration site, a TALER target sequence has been identified that contains a TALER central sequence flanked by a unique pair of N-TALER DNA-binding sites (Table 1).

TABLE 1

TALER target sequences at target integration sites in corn genome.

| SEQ ID NO: | Target site | TALE binding site 1 | TALER central sequence | TALE binding site 2 |
|---|---|---|---|---|
| 1 | TR1 | TAGGGACATGGTA GTACGAAACGAA (Nucleotides 1-25 of SEQ ID NO: 1) | GATAGAACCTACAC AGCAATACGAGAAA TGTGTAATTTGG (Nucleotides 26-65 of SEQ IDID NO: 1) | TGCTTAGCGGTAT TTATTTAAGCAC (Nucleotides 66-90 of SEQ ID NO: 1) |
| 2 | TR2 | TCATACTACATGG GTCAATAGTATA (Nucleotides 1-25 of SEQ ID NO: 2) | GGGATTCATATTAT AGGCGA (Nucleotides 26-45 of SEQ ID NO:2) | TACTATAATAATT TGTTCGTCTGCA (Nucleotides ID46-70 of SEQ ID NO: 2) |
| 3 | TR3 | GTGGGATGACGTT AATTGGCTCTGA (Nucleotides 1-25 of SEQ ID NO: 3) | GCTTCGTCCTCTTA AGGTCATGTCTTCT GTTTCCACGGCG (Nucleotides 26-65 of SEQ IDID NO: 3) | TGCATGCTACACG GTGCAAGCAGCC (Nucleotides 66-90 of SEQ ID NO: 3) |
| 4 | TR6 | TGGCATGATGAAG GCAACATGGCCA (Nucleotides 1-25 of SEQ ID NO: 4) | TGATGAATTCATCA ATCAAGCT (Nucleotides 26-47 of SEQ NO: 4) | TGGTACCTCTATT AGGTAC (Nucleotides ID48-66 of SEQ ID NO: 4) |

Previous experiments using a bacterial expression system have demonstrated that the TALER central sequences of the TR1, TR2, TR3, and TR6 target integration sites were recombined with a perfect Gin sequence by each of the pN-TALER chimeras tested (N-TALER-IV-1 and pN-TALER-IV-5) (see U.S. application Ser. No. 14/109,823, the contents of which are hereby incorporated by reference). In these previous experiments, when N-TALER reporter constructs (comprising a LacZalpha gene flanked by two N-TALER target sequences) were co-transformed with a pN-TALER expression construct, successful removal ("looping out") of the LacZalpha reporter gene via recombination was confirmed by the presence of white colonies and subsequent reporter construct sequencing. For one of the N-TALER integration target sites, the respective TR1, TR2, or TR3 TALER central sequences were flanked by TALE13 DNA-binding sites, and the second N-TALER target integration site comprised a perfect Gin recombinase central sequence flanked by TALE13 binding sites.

For in planta TALER-mediated targeted integration, donor constructs have been designed to place a perfect Gin recombinase central sequence between the respective TR1, TR2, TR3, or TR6 TALE binding sites. The design of the donor constructs targeting integration sites TR1 or TR2 also includes a GPF CDS cloned downstream of the partial DnaK site selected for targeted for integration so as to allow GFP expression in properly integrated events (see FIG. 2). The design of the donor construct targeting integration site TR3 places a perfect Gin recombinase central sequence in front of a GFP CDS lacking a start codon. Consequently, successful recombination between the donor Gin recombinase central sequence and the host genomic central sequence will result in the GFP CDS integration in-frame with the start codon of the CP4-EPSPS cassette. Design of each of the donor constructs, corresponding to target integration sites TR1, TR2, TR3, and TR6, includes a KanR gene for bacterial selection and an NptII gene for paromycin resistance in planta.

In planta TALER expression cassettes can contain a functional plant promoter (e.g., DaMV), the pN-TALER-IV-5 coding region, and a functional plant terminator (e.g., SetI). The TALE protein that can be used is the PthXho1 TALE and the RVD repeats can be substituted with the particular repeat array that binds the desired integration site target sequence. The TALE protein can be truncated at the same N-terminal positions as pN-TALER-IV-5 used in the bacterial TALER assays above. The TALE protein can have a full length C-terminus. Additionally, a plant nuclear localization sequence (NLS) can be added to the TALER C-terminus.

TABLE 2

Examples of TALER target sequences that can be used in donor constructs with perfect Gin recombinase central sequence.

| SEQ ID NO: | Target site | TALE binding site 1 | TALER central sequence | TALE binding site 2 |
|---|---|---|---|---|
| 5 | TR1 | TAGGGACATGGTA GTACGAAACGAA (Nucleotides 1-25 of SEQ ID NO: 5) | TCCAAAACCATGG TTTACAG (Nucleotides 26-45 of SEQ ID NO: 5) | TGCTTAGCGGTAT TTATTTAAGCAC (Nucleotides 46-70 of SEQ ID NO: 5) |
| 6 | TR2 | TCATACTACATGG GTCAATAGTATA (Nucleotides 1-25 of SEQ ID NO: 6) | TCCAAAACCATGG TTTACAG (Nucleotides 26-45 of SEQ ID NO: 6) | TACTATAATAATT TGTTCGTCTGCA (Nucleotides 46-70 of SEQ ID NO: 6) |
| 7 | TR3 | GTGGGATGACGTT AATTGGCTCTGA (Nucleotides 1-25 of SEQ ID NO: 7) | TCCAAAACCATGG TTTACAG (Nucleotides 26-45 of SEQ ID NO: 7) | TGCATGCTACACG GTGCAAGCAGCC (Nucleotides 46-70 of SEQ ID NO: 7) |
| 8 | TR6 | TGGCATGATGAAG GCAACATGGCCA (Nucleotides 1-25 of SEQ ID NO: 8) | TCCAAAACCATGG TTTACAG (Nucleotides 26-45 of SEQ ID NO: 8) | TGGTACCTCTATT AGGTAC (NucleotideS 46-64 of SEQ ID NO: 8) |

Seed from one or more corn lines made by transformation with pMON58401 (U.S. Pat. No. 7,919,321 and U.S. Patent Publication No. 2011/0126310), and homozygous for a single insertion of the transgene cassette, can be obtained. Using standard protocols, callus can be generated from this transgenic seed. The donor DNA and TALER expression cassettes targeting the TR1, TR2, TR3 or TR6 sites can be delivered as plasmids to the callus using a standard biolistic method, or other plant transformation protocols. Transformation using only a donor DNA construct can be used as a negative control. Post-transformation calli co-bombarded with donor DNA and TALER expression constructs targeting the preselected sites, TR1, TR2, TR3, or TR6, can be examined for GFP fluorescence. Calli co-bombarded with donor DNA and TALER expression constructs targeting the TR1, TR2, TR3, and TR6 sites, and exhibiting stable sectors on selection media containing paromycin, can be recovered and placed on regeneration media. After plants are regenerated, they can be assayed for GFP fluorescence and analyzed using known molecular techniques (e.g., PCR and emulsion PCR) to assess donor and the target site linkage.

Example 2

TALER-Mediated Targeted Integration of Exogenous DNA into a Specified Host Genomic Locus Using Recombinase-Mediated or Virus-Mediated Circularization Recombination between a single host genomic site and a corresponding site in a circular donor DNA molecule will result in integration of the entire donor DNA molecule into the host genome at the site of recombination. By contrast, recombination between a single host genomic site and a corresponding site in a linear donor DNA molecule will result in a chromosomal break. As many transformation methods employ linear DNA molecules, a method to avoid host chromosomal breakage from TALER-mediated integration of a linear donor DNA molecule is described.

Figure 3:
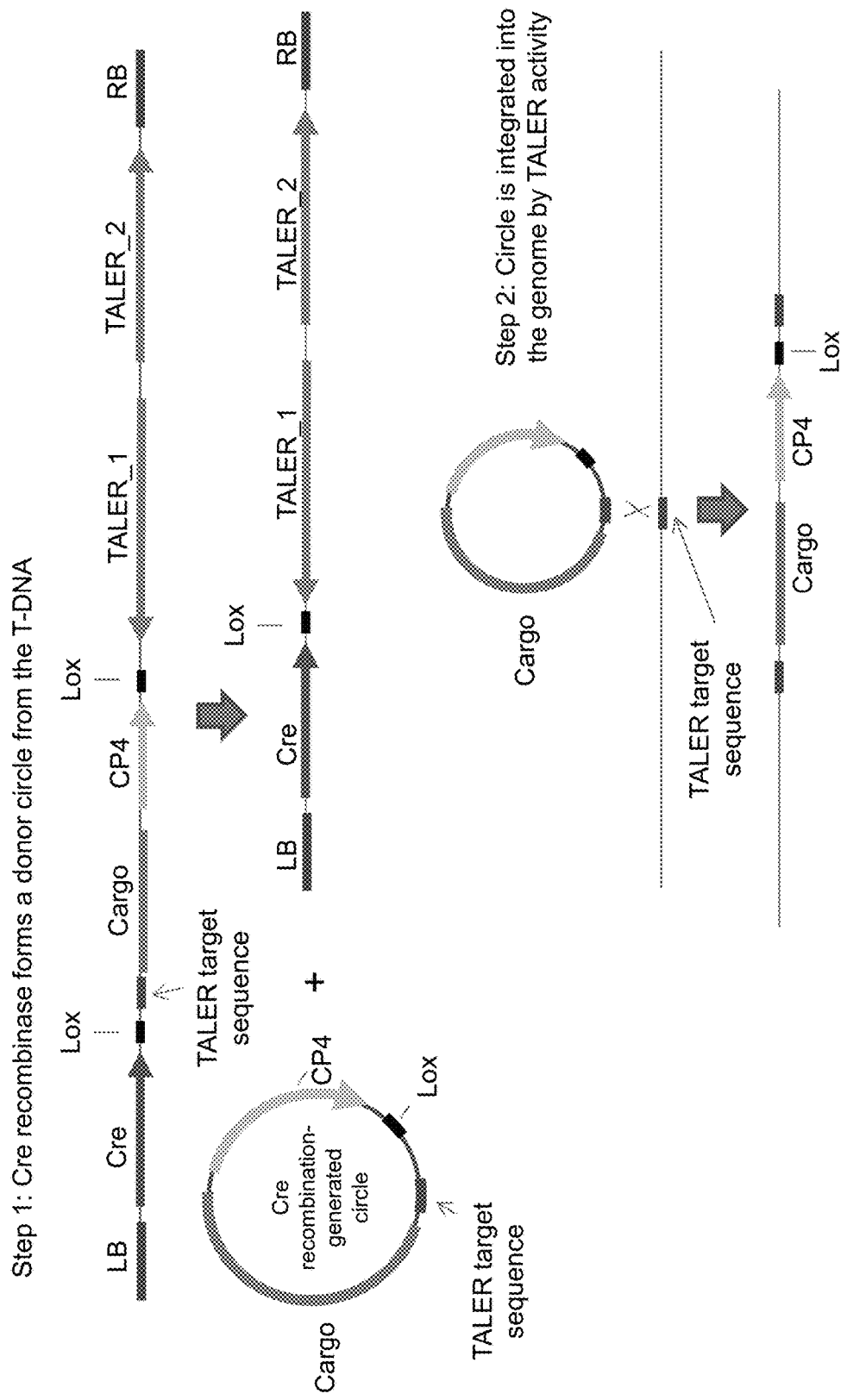
FIG. 3: A schematic representation of TALER-mediated gene-targeting using *Agrobacterium*-mediated transformation and a recombinase-generated intermediate circular DNA molecule.

An exogenous DNA sequence of interest to be integrated into a host genome (FIG. 3, "cargo"), and a suitable TALER target sequence site for TALER-mediated recombination, are flanked by recombination sites (e.g., Lox sites). The corresponding recombinase (e.g., Cre) for these flanking sites is transformed along with the linear DNA molecule, either on the same linear donor DNA molecule or separately. Recombination between the two flanking recombination sites will result in excision of the TALER target sequence and the exogenous DNA sequence of interest as an intermediate circular DNA molecule (FIG. 3). Expression of the TALER recombinase, corresponding to the TALER target sequence on the intermediate circular DNA, will then mediate recombination with the host genomic TALER target sequence at the intended integration site.

Many recombinases well known in the art can be used to form the intermediate circular DNA molecule. Non-limiting examples include Cre, Flp, phiC31, and TALERs. Recombination mediated by the Cre/Lox system is well known in the art, efficient, and can be irreversible depending on the choice of recombinase and recombinase recognition site. If two TALER sites with "perfect" sites in their TALER central sequences flank the DNA sequence of interest to be integrated, the same TALER or TALER pair can be used to create the intermediate circle and integrate it into the host genome. Because the recombination sites are constrained to be near each other by being on the same linear piece of DNA, TALER-mediated intermediate circle formation should be a very efficient.

Alternatively, the DNA construct comprising an exogenous DNA sequence of interest to be integrated into a host genome, and a suitable TALER target sequence site for TALER-mediated recombination, can also comprise viral sequences from a double-stranded RNA or DNA virus (e.g., caulimovirus) or a virus with a double-stranded replication intermediate (e.g., a geminivirus; see, e.g., Mor et al., 2003; Willment et al., 2007; Bruce et al., 2011). The corresponding replication protein for these viral sequences can be transformed along with the linear DNA molecule, either on the same linear donor DNA molecule or separately. The replication protein will mediate the formation of multiple double-stranded DNA intermediate circles comprising the TALER target sequence and the exogenous DNA sequence of interest. Expression of the TALER recombinase, corresponding to the TALER target sequence on the intermediate circular DNA, will then mediate recombination with the host genomic TALER target sequence at the intended integration site.

Many geminivirus well known in the art can be used to form the intermediate double-stranded DNA circles. Non-limiting examples include maize streak virus (MSV), bean yellow dwarf virus (BYDV), and wheat dwarf virus (WDV).

The CP4-EPSPS gene can be included in the circular donor DNA molecule to serve as a selectable marker for selection of stable transformation events (FIG. 3). However, many other selectable markers could be used. Because the intermediate circular donor DNA molecule is integrated without the other linear DNA molecules, the Cre and TALER expression cassettes can be on the same, or separate, DNA molecules. The Cre and TALER expression cassettes can be on a single T-DNA containing the Lox-flanked donor DNA molecule that will become the intermediate circle. Alternatively, the two TALER cassettes can be delivered on a separate T-DNA from the donor DNA molecule. Other possible arrangements include the Cre cassette on a separate T-DNA, the Cre cassette and one or both of the TALER expression cassettes on circular DNA, or any combination thereof. Alternatively, one or more of the Cre or TALERs can be delivered as proteins. Alternatively, one or more of the Cre or TALERs can be delivered as mRNA molecules. A preferred embodiment for plant transformation would be to use *Agrobacterium*-mediated transformation to deliver the targeting construct carrying the DNA sequence of interest. More preferably, one embodiment would be to deliver the Cre, or other recombinase and TALER molecules, as expression cassettes.

Methods similar to these have been used successfully using Cre or Flp recombinases with *Agrobacterium*-mediated transformation to insert DNA sequences of interest into plant genomic loci requiring prior insertion of Lox or Flp recombinase recognition sites. The use of those recombinases, and other specific recombinases known in the art, is limited to sites in the host genome that already possess the respective recombinase recognition sites; a limitation not shared by the methods described herein.

Example 3 pTALER-Mediated Targeted Integration of Exogenous DNA into a Specified Host Genomic Locus Using Modified Recombinase Mediated Cassette Exchange (mRMCE)

Figure 4:
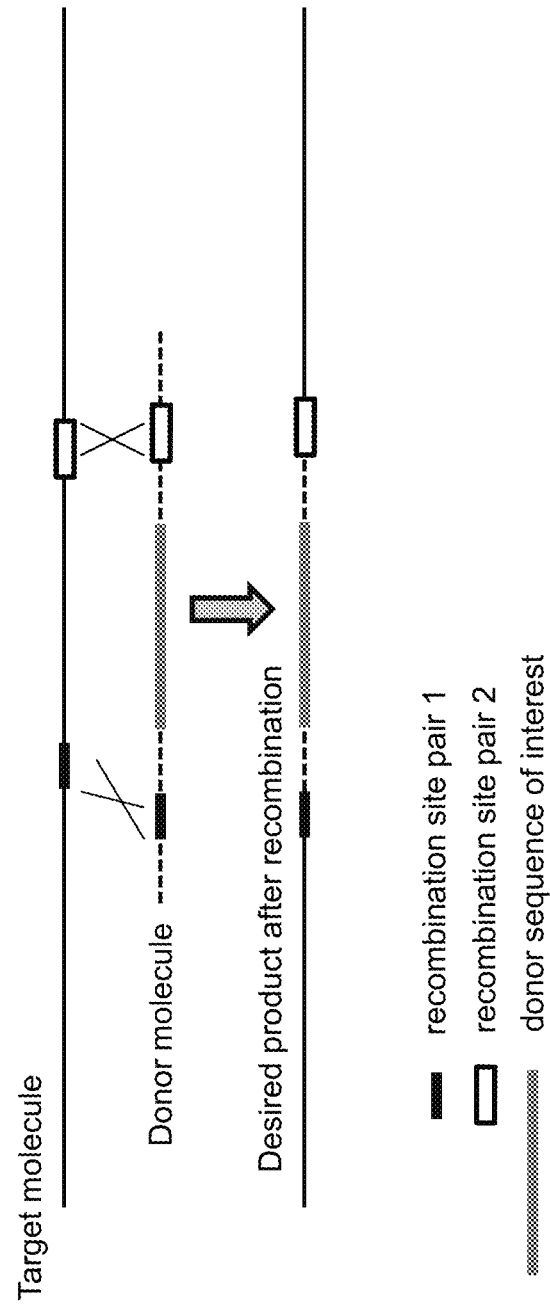
FIG. 4: A schematic representation of Recombination-Mediated Cassette Exchange (RMCE).

Recombination-mediated cassette exchange (RMCE) has been previously described as a method for inserting traits into desired locations. In short, RMCE is the use of recombinases to cause recombination at two pairs of recombination sites such that a piece of DNA flanked by these sites in a donor molecule replaces a segment in the target molecule that is flanked by a corresponding pair of recombination sites (FIG. 4). There should be one recombination site from each pair on both the donor and target molecule.

RMCE requires a pair of recombination sites in the target molecule (e.g., a chromosome) flanking the desired site of integration. This is a significant limitation because the likelihood of two recombination sites for known recombinases pre-existing at a desired genomic location is extremely low. As a result, for successful RMCE using known recombinases, a pair of recombination sites for the known recombinases must first be added to the genomic site of interest so as to enable subsequent targeted insertions.

Figure 5:
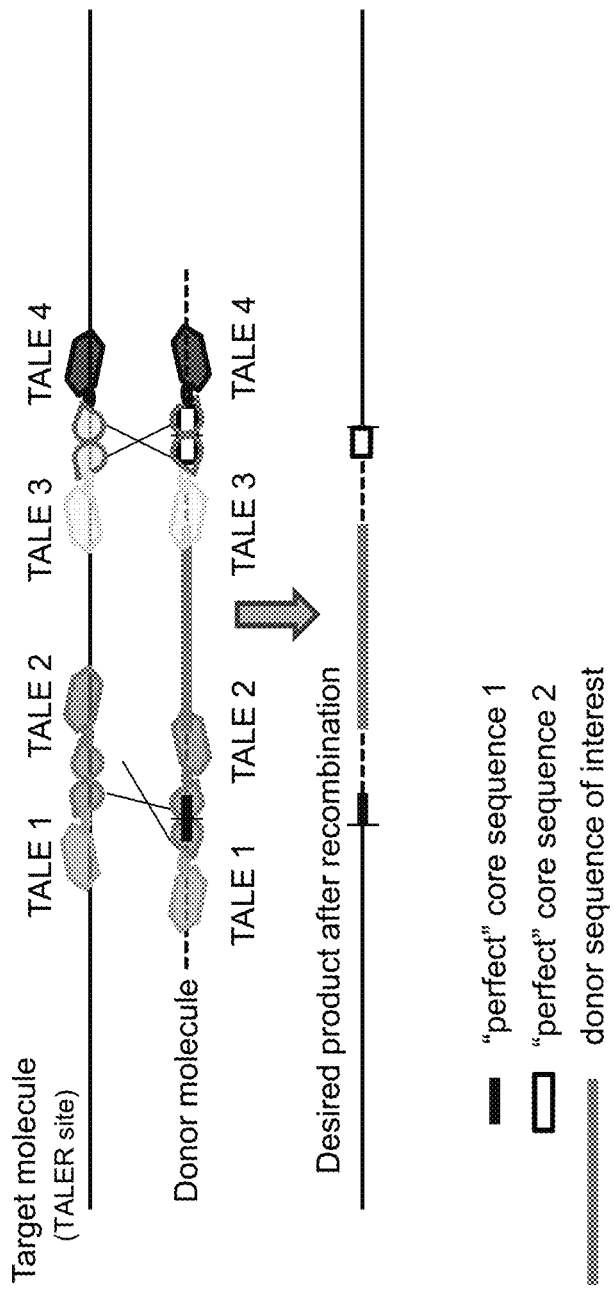
FIG. 5: A schematic representation of Modified Recombination-Mediated Cassette Exchange (mRMCE).

To overcome this limitation, a modified version of RMCE (mRMCE) is described herein which does not require recombination sites for known recombinases to be present in the host genome. Instead, pTALERs (pN-TALER or pC-TALER) can be used, thereby allowing the use of endogenous sites in a host genome to be readily used as target sites for recombination and integration of a donor DNA molecule (FIG. 5).

pTALER-mediated recombination can employ a first set of pTALERs, with a first permissive recombinase catalytic domain (i.e., GinL7C7-EE2), to recombine a first target site in the genome with a first target site in the donor. Then, a second set of pTALERs, with a second permissive recombinase catalytic domain different from the first permissive recombinase catalytic domain, can be used to mediate recombination between a second target site in the genome with a second target site in the donor. In this case, the second permissive recombinase catalytic domain can be selected to be incompatible with the first permissive recombinase catalytic domain. Alternatively, both the first and second set of pTALERs can contain the same permissive recombinase catalytic domain.

For mRMCE, TALERs are designed for a pair of endogenous sequences flanking the desired genomic site of integration and the corresponding recombination sequences in the donor molecule. At each recombination site, the TALE binding sites are in the appropriate orientation, and suitably spaced, for compatibility with their respective N-TALER or C-TALER. Given the ease of identifying and designing TALE binding sites, and the flexibility provided by permissive TALERs as described above, the requisite criteria of orientation and spacing of the TALE binding sites should not be limiting.

A key difference between the mRMCE and RMCE methods is in the selection of host genome recombination target sites. RMCE requires that the recombination target sites comprise a recombinase-specific recognition sequence, which generally requires an initial modification of the host genome to create those sequences at the desired recombination locus. By contrast, mRMCE allows for the recombination recognition sites in the host genome to be selected from pre-existing endogenous sequence. The advantage is in the ability to target any number of host genomic loci for recombination using the endogenous sequence at these sites to guide TALER and donor DNA construct design and thus facilitate efficient TALER-mediated recombination at these sites.

In cases where mRMCE uses pTALERs sets with compatible recombinase catalytic domains (e.g., pTALERs with the GinL7C7-EE2 domain), it can be desirable to have different di-nucleotides at the centers of the perfect sites and corresponding genomic loci; this increases the efficiency of directional integration of the donor DNA sequence of interest.

The mRMCE method can also be used with TALERs containing recombinase catalytic domains derived from differing serine recombinases, or other recombinases variants (e.g., gamma delta, Tn3, Sin). TALERs possessing these variant recombinase catalytic domains would be incompatible with TALERs possessing non-identical recombinase catalytic domains (i.e., Gin) and therefore would not form functional tetramers. As such, TALER sets designed with incompatible recombinase catalytic domains can enable directional integration of donor DNA molecules.

To produce targeted transformation with the mRMCE method using recombinase domain variants with altered specificity, first, a host genomic locus for targeted integration of exogenous DNA is chosen.

mRMCE with exogenous DNA first requires the identification of two pairs of TALE binding sites, in the correct orientation and spacing to enable TALER activity, flanking the target host genomic locus. Here, consideration can be given to selecting TALER target sequences with different central di-nucleotides, which can improve efficiency and be preferable if the recombinase variants to be used are compatible. Second, two recombinase variants, and their expression constructs, suitable for mediating recombination between the TALER target sequences are identified and created. Preferably, the two recombinase variants are incompatible (e.g., one is a modified Gin domain and the other is a modified Sin domain). Third, a host cell is transformed with a donor DNA molecule (e.g., a T-DNA) containing the two TALER target sequences, selected from the host genomic locus of interest, flanking the sequence to be integrated into the host genome. In the same or subsequent transformations, the TALERs are delivered into the host cell (e.g., by placing the TALER expression cassettes on the donor DNA molecule). Optionally, a counter-selectable marker can be placed on the donor DNA molecule outside the two TALER target sequences so as not to be integrated during TALER-mediated recombination. Fourth, transformation events are recovered by selection of a selectable marker contained in the donor DNA molecule or, alternatively, on a separate co-transformed DNA molecule. One skilled in the art will know suitable methods for recovering such events. Finally, transformants are screened for targeted integration events using standard molecular assays (e.g., PCR, or Southern blotting).

To produce targeted transformation with the mRMCE method using pTALERs (e.g., both pTALERs can have the GinL7C7-EE2 domains) can be followed essentially as described above with the exception of changes to the third step. Here, following selection of a targeted host genomic locus and corresponding TALE binding sites, TALER constructs containing the correct TALE binding site fused to permissive recombinase catalytic domains are created. Ideally, two incompatible recombinase domains are used (e.g., one domain is GinL7C7 and the other is a modified Tn3 domain such as that previously described (Proudfoot et al., 2011)). These TALER constructs will encode either pN-TALERs or pC-TALERs.

Example 4

Creating Genetically-Linked Mega-Loci in a Host Genome Using TALER-Mediated Targeted Integration of Exogenous DNA One utility of using TALERs to insert transgenes, or other sequences of interest, into targeted locations in a host genome is the creation of a mega-locus comprising the desired sequences. The mega-locus can have many sequences of interest (hereafter called traits), inserted into unique, separate loci in the host genome, but all genetically linked. Because they are genetically linked, they can segregate together and be transmitted to the next generation together. Small genetic distances can span large physical distances (i.e., many base pairs), therefore, multiple individual traits can be inserted at unique locations such that there is minimal or no effects on site-dependent gene expression. Such mega-loci can be built up by r-retransformation of lines containing another trait, or by independently transforming lines that do not contain all or any other traits of interest, and subsequently combining the traits onto a single chromosome by genetic recombination.

In addition TALER-mediated integration of traits, mega-loci can contain traits placed by other methods, such as nuclease-mediated targeting or positive/negative selection of homologous recombination. Additionally, the mega-loci can be on extra chromosomes (e.g., artificial chromosomes or B chromosomes).

Example 5

Creating Genetically-Linked Mega-Loci in a Host Genome Using Sequential TALER-Mediated Targeted Integration Events of Exogenous DNA in Heterologous Chromosomes, and Meiotic Recombination Placing two independent traits at specific positions on homologous chromosomes (within a genome) for independently transformed individuals, these can be crossed, and meiotic recombination will generate a chromosome with both traits. Subsequently, additional traits can be placed at sites that are at nearby genetic positions on homologous chromosomes in separate independent transformations, and these can be combined in a stepwise fashion to create chromosomes with many different traits. Traits can also be removed by meiotic recombination, or replaced with other traits put at the same or nearby sites.

In addition to meiotic recombination, TALER-mediated recombination can be used to link traits that are placed at different physical locations but identical genetic positions. For example, traits placed on either side of a centromere, or at two sites on the same side of a centromere within the recombination-free zone that surrounds centromeres, can be linked by TALER-mediated recombination between the two chromosomes at a locus between the two traits, thereby creating a mega-locus.

Example 6

Creating Marker-Free Events Using TALER-Mediated Targeted Integration of Exogenous DNA into Specified Host Genomic Loci One-Step Method.

Recovery of transgenic events often requires selection of a gene that alleviates the effect of one or more compounds applied to cells or tissue (e.g., in the media) that is toxic or otherwise prevents growth or proper development of a non-transformed event. Such markers include, for example, herbicide tolerance genes in plants. In some cases, persistence of the selectable marker is undesirable. A utility of the methodology described herein is to produce transformed events, containing a DNA sequence of interest integrated into a specific genomic locus, where any selectable marker used in the process has been removed from the genome of the selected transformed events.

Co-transformation of a cassette, encoding a selectable marker, along with a DNA sequence of interest can allow events that contain targeted DNA sequences of interest to be recovered by selection. Delivery of the selectable marker cassette can be by a method that does not facilitate its integration into the targeted genomic locus while simultaneously employing TALERs or other methods to cause the DNA sequence of interest to be integrated at said locus. Events that survive selection will have an increased chance of containing the sequence of interest. Following selection, transformants would be screened for events where the selectable marker cassette and the targeted, integrated DNA sequence of interest are unlinked. In subsequent transformant progeny, these unlinked events can independently segregate to give rise to marker-free transformants containing the integrated DNA sequence of interest at the intended target locus.

In one embodiment of this method, a circular DNA molecule, containing the DNA sequence of interest and a TALER target sequence as described above, is co-bombarded into a cell with separate TALER expression constructs and a selectable marker construct that does not contain TALER target sequences, and is therefore not targeted for genomic integration.

When using *Agrobacterium*-mediated plant transformation, the selectable marker can be delivered on a separate T-DNA from the T-DNA containing the precursor to the intermediate circle. Alternatively, the selectable marker can be on the same T-DNA that contains the precursor to the intermediate circle, as long as the selectable marker is not included in the intermediate circle.

In addition, the selectable marker can be delivered as a disrupted cassette that is repaired by removal of the intermediate circle. In this way, all events recovered, at least transiently, will have an intermediate circle, thereby increasing the likelihood of recovering selected transformants containing a targeted integration of the DNA sequence of interest.

In another embodiment of this method, the selectable marker can be targeted for integration at a different genomic locus than the DNA sequence of interest. Targeted integration of the selectable marker can be by the same method or by a different method (e.g., nuclease stimulated gene-targeting, TALER-mediated insertion, homology mediated gene-targeting) than that used to target integration of the DNA sequence of interest.

Two-Step Method.

A two-step method is contemplated to generate marker free events. For this method, the selectable marker (or other sequences used to assist in transformation or gene-targeting) is flanked by recombinase recognition sites (e.g., Lox sites). First, a donor DNA construct containing a selectable marker and the DNA sequence of interest is integrated into a chosen host genomic locus via TALER-mediated recombination. Second, following selection and identification of targeted events, these transformants can be crossed to a second transgenic plant line expressing a recombinase (e.g., Cre) that will recombine the two sites flanking the selectable marker (i.e., the Lox sites) and thus removing the intervening selectable marker sequence.

Alternatively, expression of the recombinase used to remove the selectable marker can be tissue-specific, or chemically or environmentally inducible. As such, following post-transformation selection, the recombinase can be activated and remove the sequence flanked by the recombination sites. Furthermore, the recombinase expression cassette itself can be included in the sequence to be removed.

Example 7

Genomic Rearrangements Using TALERs

Recombinases can cause genomic rearrangements by recombining sites at different locations in the genome. However, use of recombinases for directed genomic rearrangements is currently not practiced because the native recombinase target sites for known recombinases are rarely found at the desired position of genomic rearrangement. TALERs are ideal tools for solving this problem due to the flexibility in altering the specificity of the TALER to direct targeted genomic rearrangement.

As demonstrated above, only 6 to 8 bp of specificity are required in the TALER central sequence between two TALE binding sites (e.g., NNNNNNACCNNGGTNNNNNN (SEQ ID NO:9) where NN can be at a minimum AT, AA, TT, TC, or GA) for recombination to be catalyzed by pTALERs made with the GinL7C7-EE2 recombinase catalytic domain. sTALERs using the Gin domain have at most a 12 bp sequence requirement (NNNNAAACCNNGGTTTNNNN (SEQ ID NO:10) where NN can be at a minimum AT, AA, TT, TC, or GA). Because TALE binding sites are easily designed and there is considerable flexibility for the length of the TALER central sequence for some TALER variants, almost any time either sequence (SEQ ID NO:9 or SEQ ID NO:10) is encountered, a TALE set can be designed to recombine it with another such sequence elsewhere in the genome. Additional TALER variants can be developed with less or different sequence specificity, further expanding the possible sites in the genome that can be recombined for genomic rearrangement.

Additionally, since the small serine recombinases can be easily altered by molecular evolution (e.g., cycles of selection of functional variants from pools of alterations), TALERs using small serine recombinases are an ideal platform to make new recombinases targeting specific genomic loci for rearrangement.

To create specific genomic rearrangements, first, a preferred (perfect) recombinase core sequence (e.g., NNNNN-NACCNNGGTNNNNNN (SEQ ID NO:9) where NN can be at a minimum AT, AA, TT, TC, or GA for pTALERs with GinL7C7-EE2, or NNNNAAACCNNGGTTTNNNN (SEQ ID NO: 10) where NN can be at a minimum AT, AA, TT, TC, or GA for TALERs with Gin) is identified in host genomic loci where rearrangement is desired. If intergenic recombination between homologous loci is desired, the same TALER target sequence can be used on both chromosomes. Second, the appropriate TALER expression constructs, designed to bind on either side of the endogenous sequences of interest targeted for recombination, are produced. If non-homologous sites are desired, then four TALERs can be required to form a functional set. Third, these TALERs are expressed, stably or transiently, in the host organism via transformation with TALER expression constructs, TALER-encoding mRNA, or TALER proteins. Fourth, transformants are screened for the intended genomic rearrangement using standard molecular techniques (e.g., PCR, Southern blotting, or other techniques known to one of skill in the art).

Engineered genomic rearrangements can, for example, be useful for: 1. Mimicking genetic recombination (especially between sites that are very tightly linked). 2. Undoing rearrangements that differentiate genomes of relatives to facilitate introgression of useful genetic material. For example, many plant species have wild relatives with useful agronomic properties such as disease resistance. However, when the trait is brought into the domesticated variety, it brings along other genetic material that is linked to the trait. When rearrangements such as inversions differentiate the genomic regions of the relative with the useful trait from the domestic variety, meiotic recombination may not occur to unlink the undesirable genetic material. Undoing the differentiating rearrangement would allow recombination to occur and the desired trait to be cleanly introgressed into the domesticated variety. 3. Creating regions of reduced or eliminated genetic recombination. 4. Moving native traits from one genomic locus to another to allow for the creation of mega-loci of useful traits and introgressed into other lines. 5. Facilitating inter-species chromosomal exchange (e.g., recombination between a wheat chromosome and a rye chromosome to replace a portion of the wheat chromosome with the related region from the rye chromosome).

REFERENCES

The following references, to the extent that they provide exemplary procedural or other details supplementary to those set forth herein, are specifically incorporated herein by reference.

Akopian et al., *Proc Natl Acad Sci USA* 100: 8688-8691, 2003
Boch et al., *Science,* 326, 1509-1512, 2009
Bogdanove and Voytas, *Science,* 333:1843-1846, 2011
Broothaerts et al., *Nature,* 443(7026):629-633, 2005
Bruce et al., *Virol J.,* 8:561, 2011
Buchholz and Hauber, *Methods,* 53(1):102-109 2011
Dhar et al., *Cell,* 119(1):33-45, 2004
Garcia-Otin and Guillou, *Frontiers in Bioscience,* 11:1108-1136, 2006
Gelvin, *Microbiology and Molecular Biology Reviews,* 67(1):16, 2003
Gersbach et al., *Nucleic Acids Research,* 38(12):4198-4206, 2010
Gordley et al., *J. Mol. Biol.,* 367(3):802-813, 2007
Gordley et al., *PNAS,* 106(13): 5053-5058, 2009
Hellens et al., *Trends in Plant Science,* 5(10):446-451, 2000
Lida et al., *Current Opinion in Biotechnology,* 15(2):132-138, 2004
Moscou and Bogdanove, *Science,* 326:1501, 2009
Mild et al., *Methods in Plant Molecular Biology and Biotechnology,* 1993
Mor et al. *Biotechnol Bioeng.,* 81(4):430-7, 2003
Nagy, *Genesis,* 26(2):99-109, 2000
Nern et al., *Proc Natl Acad Sci USA.* 108(34):14198-203, 2011
Proudfoot et al., *PLoS One,* 6(4):e19537, 2011
Schornack et al., *J. Plant Physiology,* 163(3):256-272, 2006
Torney et al., *Nature Nanotechnology* 2:295-300, 2007
Turan and Bode, *FASEB Journal,* 25:4088-4107, 2011
Tucker et al, *Current Opinion in Structural Biology,* 15(3); 342-348, 2005
Vergunst et al., *Science,* 290(5493): 979-982, 2000
Willment et al., *J Gen Virol.,* 88(Pt 6):1831-41, 2007
You et al. *Plant Physiology,* 140(4):1205-1212, 2006
Zhu and Sadowski, *J. Biol Chem.* 270(39): 23044-23054, 1995

What is claimed is:

1. A method of integrating a nucleic acid sequence into a selected genomic locus comprising:
   a) transforming a host cell with:
      i) at least one linear donor DNA construct comprising a first TALER target sequence and an exogenous DNA sequence, wherein the donor DNA construct further comprises nucleic acid sequences that cause the formation of a circular intermediate comprising the exogenous DNA sequence and the first TALER target sequence;
      ii) at least one nucleic acid sequence encoding a TALER, wherein the TALER comprises a small serine recombinase catalytic domain and forms part of a tetramer and mediates recombination between the first TALER target sequence and a second TALER target sequence located in the host cell genome, wherein the second TALER target sequence is endogenous to the host cell genome; and b) identifying a transformed host cell comprising the donor DNA construct integrated at a selected genomic locus in said host cell wherein the first and second TALER target sequences comprise a pair of TALE binding sites flanking a recombinase core sequence, wherein the pair of TALE binding sites are spaced from about 18 bp to about 50 bp apart.

2. The method of claim 1, wherein the nucleic acid sequences that cause the formation of the circular intermediate comprise flanking recombinase recognition sites.

3. The method of claim 2, wherein the flanking recombinase recognition sites are selected from the group consisting of Cre, FLP, phiC31, and TALER recognition sites.

4. The method of claim 3, further comprising transforming a host cell with a nucleic acid sequence encoding a recombinase selected from the group consisting of Cre, FLP, phiC31, and TALER.

5. The method of claim 4, wherein the recombinase mediates recombination between the flanking recombinase recognition sites, thereby excising and circularizing an intermediate sequence comprising the exogenous DNA sequence and the first TALER target sequence.

6. The method of claim 5, wherein the excised and circularized intermediate sequence is integrated into the host cell genome by TALER-mediated recombination between the first and second TALER target sequences.

7. The method of claim 1, wherein the nucleic acid sequences that cause the formation of a circular intermediate comprise viral sequences from a double-stranded DNA virus or a virus with a double-stranded DNA replication state.

8. The method of claim 7, wherein the viral sequences comprise geminivirus or caulimovirus sequences.

9. The method of claim 7, further comprising transforming a host cell with a nucleic acid sequence encoding a replication protein from the virus.

10. The method of claim 9, wherein the replication protein mediates the formation of one or more double-stranded DNA intermediate circles comprising the exogenous DNA sequence and the first TALER target sequence.

11. The method of claim 10, wherein the one or more double-stranded DNA intermediate circles are integrated into the host cell genome by TALER-mediated recombination between the first and second TALER target sequences.

12. The method of claim 1, wherein the donor DNA construct further comprises a TALER expression construct.

13. The method of claim 1, wherein the sequence encoding a TALER is a mRNA sequence.

14. The method of claim 1, wherein transforming a host cell comprises a method selected from the group consisting of biolistic particle bombardment, electroporation, and *Agrobacterium*-mediated transformation.

15. The method of claim 1, wherein identifying a transformed host cell comprises screening for integration of the donor DNA construct within the second TALER target sequence in the host cell genome.

16. The method of claim 15, wherein screening comprises PCR, DNA sequencing, or Southern blotting.

17. The method of claim 1, wherein identifying a transformed host cell comprises selecting for the host cell based on the expression of a selectable marker.

18. The method of claim 17, wherein the selectable marker confers antibiotic resistance or herbicide tolerance.

19. The method of claim 1, wherein the TALER is selected from the group consisting of a sN-TALER, pN-TALER, sC-TALER, and pC-TALER.

20. The method of claim 1, wherein the TALER comprises a small serine recombinase catalytic domain selected from the group consisting of Gin20H106Y, GinL7C7-EE2, GinL7C7-EE3, HinB (HinH106Y), and HinC.

21. The method of claim 1, further comprising regenerating a plant from said transformed host cell or a progeny therefrom, wherein the plant comprises the donor DNA construct integrated at a selected genomic locus.

22. A method of stacking transgenic loci comprising:
   a) transforming a first host cell that comprises a first transgenic locus at a first TALER target sequence in the first host cell genome, wherein the first TALER target sequence is endogenous to the host cell genome, with:
      i) at least one donor linear DNA construct comprising a second TALER target sequence and a second transgenic locus, wherein the donor DNA construct further comprises nucleic acid sequences that cause the formation of a circular intermediate comprising the exogenous DNA sequence and the first TALER target sequence;
      ii) at least one nucleic acid sequence encoding a TALER, wherein the TALER comprises a small serine recombinase catalytic domain and forms part of a tetramer and mediates recombination between the first TALER target sequence located in the first host cell genome and the second TALER target sequence located on the donor circular DNA intermediate; and
      iii) at least one nucleic acid sequence encoding a selectable marker;
   b) selecting a transformed first host cell expressing the selectable marker; and
   c) screening the selected transformed first host cell for integration of the donor circular DNA intermediate to identify a host cell of a subsequent generation that comprises the first transgenic locus genetically linked to the second transgenic locus.

23. The method of claim 22, wherein the selectable marker confers antibiotic resistance or herbicide tolerance.

24. The method of claim 22, wherein screening comprises PCR, DNA sequencing, or Southern blotting.

25. The method of claim 22, wherein steps a) to c) are repeated 2 or more times with further transgenic host cells comprising at least a third, fourth, and fifth transgenic locus to obtain a stack of genetically linked transgenic loci arranged in cis.

26. A method for creating a transgenic marker-free cell comprising an integrated nucleic acid sequence at a selected genomic locus comprising:

a) transforming a host cell with:
  i) at least one linear donor DNA construct comprising a first TALER target sequence and an exogenous DNA sequence, wherein the donor DNA construct further comprises nucleic acid sequences that cause the formation of a circular intermediate comprising the exogenous DNA sequence and the first TALER target sequence;
  ii) at least one nucleic acid sequence encoding a TALER, wherein the TALER comprises a small serine recombinase catalytic domain and forms part of a tetramer and mediates recombination between the first TALER target sequence and a second TALER target sequence located in the host cell genome, wherein the second TALER target sequence is endogenous to the host cell genome; and
  iii) at least one nucleic acid sequence encoding a selectable marker;
b) selecting a transformed host cell expressing the selectable marker;
c) regenerating a plant from said transformed host cell, or a progeny therefrom, in the absence of selection for expression of the selectable marker;
d) screening the regenerated plant to confirm the absence of the selectable marker, wherein the plant comprises the donor DNA construct integrated at a selected genomic locus; and
e) selecting the regenerated plant comprising the donor DNA construct integrated at a selected genomic locus and not containing the selectable marker.

27. The method of claim 26, wherein the nucleic acid sequence encoding the selectable marker is a circular molecule further comprising a third TALER target sequence.

28. The method of claim 27, wherein the TALER forms part of a tetramer mediates recombination between the third TALER target sequence and a fourth TALER target sequence located in the host cell genome at a locus that is genetically-unlinked with the second TALER target sequence located in the host cell genome.

29. The method of claim 26, wherein the donor DNA construct further comprises recombinase recognition sites selected from the group consisting of Cre, FLP, phiC31, and TALER, and wherein said DNA construct is comprised within the nucleic acid sequence encoding a selectable marker.

30. The method of claim 29, further comprising transforming a host cell with a nucleic acid sequence encoding a recombinase selected from the group consisting of Cre, FLP, phiC31, and TALER.

31. The method of claim 30, wherein the recombinase mediates recombination between the flanking recombinase recognition sites thereby excising and circularizing an intermediate sequence comprising the exogenous DNA sequence and the first TALER target sequence from within the nucleic acid sequence encoding the selectable marker.

32. The method of claim 31, wherein the excised and circularized intermediate sequence is integrated into the host cell genome by TALER-mediated recombination between the first and second TALER target sequences.

33. The method of claim 26, wherein the donor DNA construct further comprises viral sequences from a double-stranded DNA virus or a virus with a double-stranded DNA replication state, and wherein said DNA construct is comprised within the nucleic acid sequence encoding a selectable marker.

34. The method of claim 33, wherein the viral sequences comprise geminivirus or caulimovirus sequences.

35. The method of claim 33, further comprising transforming a host cell with a nucleic acid sequence encoding a replication protein from the virus.

36. The method of claim 35, wherein the replication protein mediates the formation of one or more double-stranded DNA intermediate circles comprising the exogenous DNA sequence and the first TALER target sequence.

37. The method of claim 36, wherein the one or more double-stranded DNA intermediate circles are integrated into the host cell genome by TALER-mediated recombination between the first and second TALER target sequences.

38. The method of claim 26, wherein screening comprises PCR, DNA sequencing, or Southern blotting.

39. The method of claim 26, wherein the selectable marker confers antibiotic resistance or herbicide tolerance.

40. The method of claim 1, wherein the at least one linear donor DNA construct further comprises a selectable marker, wherein the selectable marker is not located between the nucleic acid sequences that cause the formation of the circular intermediate, whereby the circular intermediate does not comprise the selectable marker.

41. The method of claim 22, wherein the at least one nucleic acid sequence encoding a selectable marker is provided on the at least one donor linear DNA construct, wherein the selectable marker is not located between the nucleic acid sequences that cause the formation of the circular intermediate, whereby the circular intermediate does not comprise the selectable marker.

42. The method of claim 26, wherein the at least one nucleic acid sequence encoding a selectable marker is provided on the at least one donor linear DNA construct, wherein the selectable marker is not located between the nucleic acid sequences that cause the formation of the circular intermediate, whereby the circular intermediate does not comprise the selectable marker.

* * * * *